United States Patent
Franklin et al.

(10) Patent No.: US 9,241,819 B2
(45) Date of Patent: Jan. 26, 2016

(54) IMPLANTABLE DEVICE TO PROTECT TUBING FROM PUNCTURE

(71) Applicant: Apollo Endosurgery, Inc., Austin, TX (US)

(72) Inventors: Ethan Franklin, Goleta, CA (US); Christopher R. Deuel, Somerville, MA (US)

(73) Assignee: Apollo Endosurgery, Inc., Austin, TX (US)

( * ) Notice: Subject to any disclaimer, the term of this patent is extended or adjusted under 35 U.S.C. 154(b) by 0 days.

(21) Appl. No.: 14/076,606

(22) Filed: Nov. 11, 2013

(65) Prior Publication Data

US 2014/0066697 A1 Mar. 6, 2014

Related U.S. Application Data

(63) Continuation of application No. 13/019,238, filed on Feb. 1, 2011, now abandoned, which is a continuation-in-part of application No. 12/771,609, filed on Apr. 30, 2010, now Pat. No. 8,992,415.

(51) Int. Cl.
*A61F 5/00* (2006.01)
*A61M 39/02* (2006.01)
*A61M 39/12* (2006.01)
*A61M 39/10* (2006.01)

(52) U.S. Cl.
CPC .............. *A61F 5/0063* (2013.01); *A61F 5/0056* (2013.01); *A61M 39/0208* (2013.01); *A61M 39/12* (2013.01); *A61M 2039/0226* (2013.01); *A61M 2039/1066* (2013.01)

(58) Field of Classification Search
CPC ............... A61F 5/0063; A61F 5/0056; A61M 39/0208; A61M 39/12; A61M 2039/0226; A61M 2039/1066; F16L 57/00; F16L 58/1063
USPC .............................. 600/37; 138/110; 604/263, 604/288.01–288.04, 523–527
See application file for complete search history.

(56) References Cited

U.S. PATENT DOCUMENTS 586,113 A 7/1897 Bott
982,482 A 1/1911 Donelly (Continued)

FOREIGN PATENT DOCUMENTS

EP 0343910 A2 11/1989
EP 0611561 8/1994

(Continued)

OTHER PUBLICATIONS

Autumn K. et al.; 'Evidence of Van Der Waals Adhesion in Gecko Setae'; PNAS; vol. 99; No. 19; pp. 12252-12256; Sep. 17, 2012.

(Continued)

*Primary Examiner* — Jacqueline Cheng
*Assistant Examiner* — Kaylee Wilson
(74) *Attorney, Agent, or Firm* — Gordon & Jacobson, P.C.

(57) ABSTRACT

An implantable device used in a gastric band system includes an access port, a tube coupled to the access port, and a shielding device covering a portion of the tube. The shielding device is positioned adjacent to the access port and covers the end of the tube coupled to the access port. The shielding device is made from a puncture resistant material, to protect the tube from puncture by a misplaced syringe needle inserted by a physician.

18 Claims, 15 Drawing Sheets

(56) References Cited

U.S. PATENT DOCUMENTS

| | | |
|---|---|---|
| 2,163,048 A | 6/1939 | McKee |
| 2,737,954 A | 3/1956 | Knapp |
| 2,829,671 A | 4/1958 | Ernst |
| 3,109,461 A | 11/1963 | Wolff |
| 3,371,352 A | 3/1968 | Siposs |
| 3,569,660 A | 3/1971 | Houldcroft |
| 3,587,115 A | 6/1971 | Shiley |
| 3,596,660 A | 8/1971 | Melone |
| 3,667,081 A | 6/1972 | Burger |
| 3,688,764 A | 9/1972 | Reed |
| 3,731,352 A | 5/1973 | Okamoto |
| 3,840,018 A | 10/1974 | Heifetz |
| 3,958,562 A | 5/1976 | Hakim |
| 3,971,376 A | 7/1976 | Wichterle |
| 4,019,499 A | 4/1977 | Fitzgerald |
| 4,118,805 A | 10/1978 | Reimels |
| 4,151,835 A | 5/1979 | Copeland |
| 4,161,943 A | 7/1979 | Nogier |
| 4,164,943 A | 8/1979 | Hill |
| 4,190,040 A | 2/1980 | Schulte |
| 4,233,992 A | 11/1980 | Bisping |
| 4,265,252 A | 5/1981 | Chubbuck |
| 4,280,722 A | 7/1981 | Guptil |
| 4,323,727 A * | 4/1982 | Berg .............................. 174/135 |
| 4,413,985 A | 11/1983 | Wellner |
| 4,474,572 A | 10/1984 | McNaughton |
| 4,502,335 A | 3/1985 | Wamstad |
| 4,543,088 A | 9/1985 | Bootman |
| 4,557,722 A | 12/1985 | Harris |
| 4,569,675 A | 2/1986 | Prosl |
| 4,588,394 A | 5/1986 | Schulte |
| 4,592,339 A | 6/1986 | Kuzmak |
| 4,592,355 A | 6/1986 | Antebi |
| 4,634,427 A | 1/1987 | Hannula |
| 4,655,765 A | 4/1987 | Swift |
| 4,673,394 A | 6/1987 | Fenton |
| 4,692,146 A | 9/1987 | Hilger |
| 4,696,288 A | 9/1987 | Kuzmak |
| 4,704,103 A | 11/1987 | Stoeber |
| 4,710,174 A | 12/1987 | Moden |
| 4,738,657 A | 4/1988 | Hancock |
| 4,767,410 A | 8/1988 | Moden |
| 4,772,270 A | 9/1988 | Wiita |
| 4,778,452 A | 10/1988 | Moden |
| 4,781,680 A | 11/1988 | Redmond |
| 4,796,641 A | 1/1989 | Mills |
| 4,802,885 A | 2/1989 | Weeks |
| 4,832,054 A | 5/1989 | Bark |
| 4,840,615 A | 6/1989 | Hancock |
| 4,850,227 A | 7/1989 | Luettgen |
| 4,858,623 A | 8/1989 | Bradshaw |
| 4,861,341 A | 8/1989 | Woodburn |
| 4,881,939 A | 11/1989 | Newman |
| 4,886,501 A | 12/1989 | Johnston |
| 4,902,278 A | 2/1990 | Maget |
| 4,904,241 A | 2/1990 | Bark |
| 4,913,702 A | 4/1990 | Yum |
| 4,915,690 A | 4/1990 | Cone |
| 4,929,230 A | 5/1990 | Pfleger |
| 4,929,236 A | 5/1990 | Sampson |
| 4,966,588 A | 10/1990 | Rayman |
| 4,967,755 A | 11/1990 | Pohndorf |
| 4,978,338 A | 12/1990 | Melsky |
| 5,006,115 A | 4/1991 | McDonald |
| 5,013,298 A | 5/1991 | Moden |
| 5,026,344 A | 6/1991 | Dijkstra |
| 5,041,098 A | 8/1991 | Loiterman |
| 5,045,060 A | 9/1991 | Melsky |
| 5,074,868 A | 12/1991 | Kuzmak |
| 5,090,954 A | 2/1992 | Geary |
| 5,092,897 A | 3/1992 | Forte |
| 5,094,244 A | 3/1992 | Callahan |
| 5,108,377 A | 4/1992 | Cone |
| 5,125,408 A | 6/1992 | Basser |
| 5,133,753 A | 7/1992 | Bark |
| 5,137,529 A | 8/1992 | Watson |
| 5,147,483 A | 9/1992 | Melsky |
| 5,152,747 A | 10/1992 | Olivier |
| 5,167,638 A | 12/1992 | Felix |
| 5,185,003 A | 2/1993 | Brethauer |
| 5,207,644 A | 5/1993 | Strecker |
| 5,213,574 A | 5/1993 | Tucker |
| 5,226,429 A | 7/1993 | Kuzmak |
| 5,226,894 A | 7/1993 | Haber |
| 5,250,026 A | 10/1993 | Ehrlich |
| 5,273,537 A | 12/1993 | Haskvitz |
| 5,281,205 A | 1/1994 | McPherson |
| 5,284,479 A | 2/1994 | de Jong |
| 5,318,545 A | 6/1994 | Tucker |
| 5,336,194 A | 8/1994 | Polaschegg |
| 5,337,747 A | 8/1994 | Neftel |
| 5,360,407 A | 11/1994 | Leonard |
| 5,368,040 A | 11/1994 | Carney |
| 5,387,192 A | 2/1995 | Glantz |
| 5,391,164 A | 2/1995 | Giampapa |
| 5,449,368 A | 9/1995 | Kuzmak |
| 5,476,460 A | 12/1995 | Montalvo |
| 5,514,174 A | 5/1996 | Heil |
| 5,540,648 A | 7/1996 | Yoon |
| 5,556,388 A | 9/1996 | Johlin |
| 5,558,641 A | 9/1996 | Glantz |
| 5,562,617 A | 10/1996 | Finch |
| 5,571,104 A | 11/1996 | Li |
| 5,575,777 A | 11/1996 | Cover |
| 5,582,212 A | 12/1996 | Tanzosh |
| 5,601,604 A | 2/1997 | Vincent |
| 5,637,102 A | 6/1997 | Tolkoff |
| 5,653,755 A | 8/1997 | Ledergerber |
| 5,658,298 A | 8/1997 | Vincent |
| 5,674,397 A | 10/1997 | Pawlak |
| 5,683,447 A | 11/1997 | Bush |
| 5,688,237 A | 11/1997 | Rozga |
| 5,695,490 A | 12/1997 | Flaherty |
| 5,716,342 A | 2/1998 | Dumbraveanu |
| 5,718,682 A | 2/1998 | Tucker |
| 5,722,957 A | 3/1998 | Steinbach |
| 5,748,200 A | 5/1998 | Funahashi |
| 5,810,735 A | 9/1998 | Halperin |
| 5,814,019 A | 9/1998 | Steinbach |
| 5,833,654 A | 11/1998 | Powers |
| 5,843,033 A | 12/1998 | Ropiak |
| RE36,176 E | 3/1999 | Kuzmak |
| 5,883,654 A | 3/1999 | Katsuyama |
| 5,902,598 A | 5/1999 | Chen |
| 5,906,596 A | 5/1999 | Tallarida |
| 5,910,149 A | 6/1999 | Kuzmak |
| 5,911,704 A | 6/1999 | Humes |
| 5,931,829 A | 8/1999 | Burbank |
| 5,932,460 A | 8/1999 | Mills |
| 5,935,083 A | 8/1999 | Williams |
| 5,938,669 A | 8/1999 | Klaiber |
| 5,951,512 A | 9/1999 | Dalton |
| 6,024,704 A | 2/2000 | Meador |
| 6,030,369 A | 2/2000 | Engelson |
| 6,039,712 A | 3/2000 | Fogarty |
| 6,068,622 A | 5/2000 | Sater |
| 6,074,341 A | 6/2000 | Anderson |
| 6,090,066 A | 7/2000 | Schnell |
| 6,098,405 A | 8/2000 | Miyata |
| 6,102,678 A | 8/2000 | Peclat |
| 6,102,922 A | 8/2000 | Jakobsson |
| 6,123,700 A | 9/2000 | Mills |
| 6,152,885 A | 11/2000 | Taepke |
| 6,171,252 B1 | 1/2001 | Roberts |
| 6,183,449 B1 | 2/2001 | Sibbitt |
| 6,213,973 B1 | 4/2001 | Eliasen |
| 6,221,024 B1 | 4/2001 | Miesel |
| 6,234,973 B1 | 5/2001 | Meador |
| 6,258,079 B1 | 7/2001 | Burbank |
| 6,264,676 B1 | 7/2001 | Gellman |
| 6,270,475 B1 | 8/2001 | Bestetti |
| 6,283,949 B1 | 9/2001 | Roorda |
| 6,321,124 B1 | 11/2001 | Cigaina |
| 6,349,740 B1 | 2/2002 | Cho |

(56) References Cited

U.S. PATENT DOCUMENTS

| | | |
|---|---|---|
| 6,432,040 B1 | 8/2002 | Meah |
| 6,450,946 B1 | 9/2002 | Forsell |
| 6,453,907 B1 | 9/2002 | Forsell |
| 6,454,699 B1 | 9/2002 | Forsell |
| 6,459,917 B1 | 10/2002 | Gowda |
| 6,461,293 B1 | 10/2002 | Forsell |
| 6,464,628 B1 | 10/2002 | Forsell |
| 6,470,213 B1 | 10/2002 | Alley |
| 6,470,892 B1 | 10/2002 | Forsell |
| 6,478,783 B1 | 11/2002 | Moorehead |
| 6,511,490 B2 | 1/2003 | Robert |
| 6,547,801 B1 | 4/2003 | Dargent |
| 6,563,045 B2 | 5/2003 | Goett |
| 6,572,587 B2 | 6/2003 | Lerman et al. |
| 6,589,184 B2 | 7/2003 | Noren |
| 6,648,849 B2 | 11/2003 | Tenhuisen |
| 6,666,845 B2 | 12/2003 | Hooper |
| 6,689,100 B2 | 2/2004 | Connelly |
| 6,723,053 B2 | 4/2004 | Ackerman |
| 6,733,519 B2 | 5/2004 | Lashinski |
| 6,792,309 B1 | 9/2004 | Noren |
| 6,810,880 B1 | 11/2004 | Jennings |
| 6,813,964 B1 | 11/2004 | Clark |
| 6,860,857 B2 | 3/2005 | Noren |
| 6,915,162 B2 | 7/2005 | Noren |
| 6,921,267 B2 | 7/2005 | Van |
| 6,929,631 B1 | 8/2005 | Brugger |
| 6,939,299 B1 | 9/2005 | Petersen |
| 6,953,444 B2 | 10/2005 | Rosenberg |
| 6,964,204 B2 | 11/2005 | Clark |
| 6,966,875 B1 | 11/2005 | Longobardi |
| 6,997,914 B2 | 2/2006 | Smith |
| 7,017,583 B2 | 3/2006 | Forsell |
| 7,020,531 B1 | 3/2006 | Colliou |
| 7,056,286 B2 | 6/2006 | Ravenscroft |
| 7,063,669 B2 | 6/2006 | Brawner |
| 7,073,387 B2 | 7/2006 | Zdeblick |
| 7,082,843 B2 | 8/2006 | Clark |
| 7,131,945 B2 | 11/2006 | Fink |
| 7,144,400 B2 | 12/2006 | Byrum |
| 7,149,587 B2 | 12/2006 | Wardle |
| 7,191,007 B2 | 3/2007 | Desai |
| 7,195,774 B2 | 3/2007 | Carvalho |
| 7,198,066 B2 | 4/2007 | Kagenow |
| 7,223,239 B2 | 5/2007 | Schulze |
| 7,226,419 B2 | 6/2007 | Lane |
| 7,261,003 B2 | 8/2007 | McDonald |
| 7,267,645 B2 | 9/2007 | Anderson |
| 7,282,023 B2 | 10/2007 | Frering |
| 7,311,716 B2 | 12/2007 | Byrum |
| 7,311,717 B2 | 12/2007 | Egle |
| 7,351,198 B2 | 4/2008 | Byrum |
| 7,351,226 B1 | 4/2008 | Herskowitz |
| 7,351,240 B2 | 4/2008 | Hassler |
| 7,353,747 B2 | 4/2008 | Swayze |
| 7,364,542 B2 | 4/2008 | Jambor |
| 7,367,937 B2 | 5/2008 | Jambor |
| 7,374,557 B2 | 5/2008 | Conlon |
| 7,374,565 B2 | 5/2008 | Hassler |
| 7,390,294 B2 | 6/2008 | Hassler |
| 7,413,547 B1 | 8/2008 | Lichtscheidl |
| 7,416,528 B2 | 8/2008 | Crawford |
| 7,437,951 B2 | 10/2008 | McDonald |
| 7,438,718 B2 | 10/2008 | Milliman |
| 7,445,614 B2 | 11/2008 | Bunodiere |
| 7,468,038 B2 | 12/2008 | Ye |
| 7,500,944 B2 | 3/2009 | Byrum |
| 7,510,530 B2 | 3/2009 | Hashimoto |
| 7,530,943 B2 | 5/2009 | Lechner |
| 7,553,298 B2 | 6/2009 | Hunt |
| 7,561,916 B2 | 7/2009 | Hunt |
| 7,580,746 B2 | 8/2009 | Gilkerson |
| 7,591,185 B1 | 9/2009 | Mothilal |
| 7,593,777 B2 | 9/2009 | Gerber |
| 7,634,319 B2 | 12/2009 | Schneider |
| 7,651,483 B2 | 1/2010 | Byrum |
| 7,658,196 B2 | 2/2010 | Ferreri |
| 7,699,770 B2 | 4/2010 | Hassler |
| 7,708,722 B2 | 5/2010 | Glenn |
| 7,762,998 B2 | 7/2010 | Birk |
| 7,762,999 B2 | 7/2010 | Byrum |
| 7,775,215 B2 | 8/2010 | Hassler |
| 7,775,966 B2 | 8/2010 | Dlugos |
| 7,811,275 B2 | 10/2010 | Birk |
| 7,850,660 B2 | 12/2010 | Uth |
| 7,862,546 B2 | 1/2011 | Conlon |
| 7,909,754 B2 | 3/2011 | Hassler |
| 7,909,804 B2 | 3/2011 | Stats |
| 8,007,474 B2 | 8/2011 | Uth |
| 2001/0052141 A1 | 12/2001 | Andersen |
| 2002/0013545 A1 | 1/2002 | Soltanpour |
| 2002/0058969 A1 | 5/2002 | Noren |
| 2002/0087147 A1 | 7/2002 | Hooper |
| 2002/0095181 A1 | 7/2002 | Beyar |
| 2002/0139208 A1 | 10/2002 | Yatskov |
| 2002/0198548 A1 | 12/2002 | Robert |
| 2003/0045800 A1 | 3/2003 | Noren |
| 2003/0045910 A1 | 3/2003 | Sorensen |
| 2003/0073880 A1 | 4/2003 | Polsky |
| 2003/0078506 A1 | 4/2003 | Noren |
| 2003/0139690 A1 | 7/2003 | Aebli |
| 2004/0064110 A1 | 4/2004 | Forsell |
| 2004/0065615 A1 | 4/2004 | Hooper |
| 2004/0068233 A1 | 4/2004 | DiMatteo |
| 2004/0082908 A1 | 4/2004 | Whitehurst |
| 2004/0111050 A1 | 6/2004 | Smedley |
| 2004/0204692 A1 | 10/2004 | Eliasen |
| 2004/0254536 A1 | 12/2004 | Conlon |
| 2004/0254537 A1 | 12/2004 | Conlon |
| 2004/0260229 A1 | 12/2004 | Meir |
| 2004/0260319 A1 | 12/2004 | Egle |
| 2004/0267288 A1 | 12/2004 | Byrum |
| 2004/0267291 A1 | 12/2004 | Byrum |
| 2004/0267292 A1 | 12/2004 | Byrum |
| 2004/0267293 A1 | 12/2004 | Byrum |
| 2004/0267377 A1 | 12/2004 | Egle |
| 2005/0010177 A1 | 1/2005 | Tsai |
| 2005/0049578 A1 | 3/2005 | Tu |
| 2005/0070875 A1 | 3/2005 | Kulessa |
| 2005/0070937 A1 | 3/2005 | Jambor |
| 2005/0085778 A1 | 4/2005 | Parks |
| 2005/0092093 A1 | 5/2005 | Kang |
| 2005/0131325 A1 | 6/2005 | Chen |
| 2005/0131352 A1 | 6/2005 | Conlon |
| 2005/0131383 A1 | 6/2005 | Chen |
| 2005/0148956 A1 | 7/2005 | Conlon |
| 2005/0149143 A1 | 7/2005 | Libbus |
| 2005/0209573 A1 | 9/2005 | Brugger |
| 2005/0240155 A1 | 10/2005 | Conlon |
| 2005/0240156 A1 | 10/2005 | Conlon |
| 2005/0267500 A1 | 12/2005 | Hassler |
| 2005/0277899 A1 | 12/2005 | Conlon |
| 2005/0283041 A1 | 12/2005 | Egle |
| 2005/0283118 A1 | 12/2005 | Uth |
| 2005/0283119 A1 | 12/2005 | Uth |
| 2006/0074439 A1 | 4/2006 | Garner |
| 2006/0122578 A1 | 6/2006 | Lord |
| 2006/0161186 A1 | 7/2006 | Hassler |
| 2006/0173423 A1 | 8/2006 | Conlon |
| 2006/0173424 A1 | 8/2006 | Conlon |
| 2006/0178647 A1 | 8/2006 | Stats |
| 2006/0178648 A1 | 8/2006 | Barron |
| 2006/0184141 A1 | 8/2006 | Smith |
| 2006/0189887 A1 | 8/2006 | Hassler |
| 2006/0189888 A1 | 8/2006 | Hassler |
| 2006/0190039 A1 | 8/2006 | Birk |
| 2006/0199997 A1 | 9/2006 | Hassler |
| 2006/0211912 A1 | 9/2006 | Dlugos |
| 2006/0211913 A1 | 9/2006 | Dlugos |
| 2006/0211914 A1 | 9/2006 | Hassler |
| 2006/0217668 A1 | 9/2006 | Schulze |
| 2006/0217673 A1 | 9/2006 | Schulze |
| 2006/0235445 A1 | 10/2006 | Birk |
| 2006/0235448 A1 | 10/2006 | Roslin |

(56) References Cited

U.S. PATENT DOCUMENTS

| | | |
|---|---|---|
| 2006/0247539 A1 | 11/2006 | Schugt |
| 2006/0266128 A1 | 11/2006 | Clark |
| 2006/0293625 A1 | 12/2006 | Hunt |
| 2006/0293626 A1 | 12/2006 | Byrum |
| 2006/0293627 A1 | 12/2006 | Byrum |
| 2006/0293628 A1 | 12/2006 | Hunt |
| 2007/0010790 A1 | 1/2007 | Byrum |
| 2007/0015954 A1 | 1/2007 | Dlugos |
| 2007/0015955 A1 | 1/2007 | Tsonton |
| 2007/0016231 A1 | 1/2007 | Jambor |
| 2007/0027356 A1 | 2/2007 | Ortiz |
| 2007/0038255 A1 | 2/2007 | Kieval |
| 2007/0060959 A1 | 3/2007 | Salo |
| 2007/0073250 A1 | 3/2007 | Schneiter |
| 2007/0078391 A1 | 4/2007 | Wortley |
| 2007/0088336 A1 | 4/2007 | Dalton |
| 2007/0088391 A1 | 4/2007 | McAlexander |
| 2007/0129765 A1 | 6/2007 | Gilkerson |
| 2007/0135758 A1 | 6/2007 | Childers |
| 2007/0149947 A1 | 6/2007 | Byrum |
| 2007/0156013 A1 | 7/2007 | Birk |
| 2007/0158769 A1 | 7/2007 | You |
| 2007/0161958 A1 | 7/2007 | Glenn |
| 2007/0167672 A1 | 7/2007 | Dlugos |
| 2007/0173685 A1 | 7/2007 | Jambor |
| 2007/0185462 A1 | 8/2007 | Byrum |
| 2007/0191717 A1 | 8/2007 | Rosen |
| 2007/0205384 A1 | 9/2007 | Kurosawa |
| 2007/0208313 A1 | 9/2007 | Conlon |
| 2007/0213837 A1 | 9/2007 | Ferreri |
| 2007/0219510 A1 | 9/2007 | Zinn |
| 2007/0235083 A1 | 10/2007 | Dlugos |
| 2007/0250086 A1 | 10/2007 | Wiley |
| 2007/0255165 A1 | 11/2007 | Uesugi |
| 2007/0255234 A1 | 11/2007 | Haase |
| 2007/0265666 A1 | 11/2007 | Roberts |
| 2007/0282196 A1 | 12/2007 | Birk |
| 2007/0293829 A1 | 12/2007 | Conlon |
| 2008/0009680 A1 | 1/2008 | Hassler |
| 2008/0015406 A1 | 1/2008 | Dlugos |
| 2008/0039772 A1 | 2/2008 | Chantriaux |
| 2008/0058632 A1 | 3/2008 | Tai |
| 2008/0097496 A1 | 4/2008 | Chang |
| 2008/0114308 A1 | 5/2008 | Di |
| 2008/0119798 A1 | 5/2008 | Chantriaux |
| 2008/0243093 A1 | 10/2008 | Kalpin |
| 2008/0249806 A1 | 10/2008 | Dlugos |
| 2008/0250340 A1 | 10/2008 | Dlugos |
| 2008/0250341 A1 | 10/2008 | Dlugos |
| 2008/0255403 A1 | 10/2008 | Voegele |
| 2008/0255414 A1 | 10/2008 | Voegele |
| 2008/0255425 A1 | 10/2008 | Voegele |
| 2008/0255459 A1 | 10/2008 | Voegele |
| 2008/0255537 A1 | 10/2008 | Voegele |
| 2008/0281412 A1 | 11/2008 | Smith |
| 2008/0287969 A1 | 11/2008 | Tsonton |
| 2008/0287974 A1 | 11/2008 | Widenhouse |
| 2008/0312553 A1 | 12/2008 | Timmons |
| 2008/0319435 A1 | 12/2008 | Rioux |
| 2009/0018608 A1 | 1/2009 | Schwartz |
| 2009/0048524 A1 | 2/2009 | Wildau |
| 2009/0054914 A1 | 2/2009 | Lechner |
| 2009/0062825 A1 | 3/2009 | Pool |
| 2009/0071258 A1 | 3/2009 | Kouda |
| 2009/0076466 A1 | 3/2009 | Quebbemann |
| 2009/0082757 A1 | 3/2009 | Rogers |
| 2009/0082793 A1 | 3/2009 | Birk |
| 2009/0093768 A1 | 4/2009 | Conlon |
| 2009/0099538 A1 | 4/2009 | Paganon |
| 2009/0105735 A1 | 4/2009 | Stam |
| 2009/0112308 A1 | 4/2009 | Kassem |
| 2009/0118572 A1 | 5/2009 | Lechner |
| 2009/0149874 A1 | 6/2009 | Ortiz |
| 2009/0157106 A1 | 6/2009 | Marcotte |
| 2009/0157107 A1 | 6/2009 | Kierath |
| 2009/0157113 A1 | 6/2009 | Marcotte |
| 2009/0171375 A1 | 7/2009 | Coe |
| 2009/0171378 A1 | 7/2009 | Coe |
| 2009/0171379 A1 | 7/2009 | Coe |
| 2009/0192404 A1 | 7/2009 | Ortiz |
| 2009/0192415 A1 | 7/2009 | Ortiz |
| 2009/0192533 A1 | 7/2009 | Dlugos |
| 2009/0192534 A1 | 7/2009 | Ortiz |
| 2009/0192541 A1 | 7/2009 | Ortiz |
| 2009/0198261 A1 | 8/2009 | Schweikert |
| 2009/0202387 A1 | 8/2009 | Dlugos |
| 2009/0204131 A1 | 8/2009 | Ortiz |
| 2009/0204132 A1 | 8/2009 | Ortiz |
| 2009/0209995 A1 | 8/2009 | Byrum |
| 2009/0216255 A1 | 8/2009 | Coe |
| 2009/0221974 A1 | 9/2009 | Paganon |
| 2009/0222031 A1 | 9/2009 | Axelsson |
| 2009/0222065 A1 | 9/2009 | Dlugos |
| 2009/0227862 A1 | 9/2009 | Smith |
| 2009/0228028 A1 | 9/2009 | Coe |
| 2009/0228072 A1 | 9/2009 | Coe |
| 2009/0248125 A1 | 10/2009 | Brostrom |
| 2009/0248126 A1 | 10/2009 | Nippoldt |
| 2009/0254052 A1 | 10/2009 | Birk |
| 2009/0259190 A1 | 10/2009 | Birk |
| 2009/0259191 A1 | 10/2009 | Birk |
| 2009/0259231 A1 | 10/2009 | Birk |
| 2009/0264901 A1 | 10/2009 | Franklin |
| 2009/0270904 A1 | 10/2009 | Birk |
| 2009/0299216 A1 | 12/2009 | Chen |
| 2009/0299672 A1 | 12/2009 | Zhang |
| 2009/0306462 A1 | 12/2009 | Lechner |
| 2009/0308169 A1 | 12/2009 | Mothilal |
| 2010/0087843 A1 | 4/2010 | Bertolote |
| 2010/0100079 A1 | 4/2010 | Berkcan |
| 2010/0114149 A1 | 5/2010 | Albrecht |
| 2010/0130941 A1 | 5/2010 | Conlon |
| 2010/0152532 A1 | 6/2010 | Marcotte |
| 2010/0191271 A1 | 7/2010 | Lau |
| 2010/0211085 A1 | 8/2010 | Uth |
| 2010/0217198 A1 | 8/2010 | Franklin |
| 2010/0217199 A1 | 8/2010 | Uth |
| 2010/0217200 A1 | 8/2010 | Uth |
| 2010/0228080 A1 | 9/2010 | Tavori |
| 2010/0234808 A1 | 9/2010 | Uth |
| 2011/0054407 A1 | 3/2011 | Olroyd |
| 2011/0082426 A1 | 4/2011 | Conlon |
| 2011/0306826 A1 | 12/2011 | Franklin |
| 2012/0109068 A1 | 5/2012 | Vendely |
| 2012/0123198 A1 | 5/2012 | Marcotte |

FOREIGN PATENT DOCUMENTS

| | | |
|---|---|---|
| EP | 1346753 | 9/2003 |
| EP | 1488824 A1 | 12/2004 |
| EP | 1543861 A1 | 6/2005 |
| EP | 1547643 | 6/2005 |
| EP | 1591140 A1 | 11/2005 |
| EP | 1736194 A1 | 12/2006 |
| EP | 1736195 | 12/2006 |
| EP | 1736196 | 12/2006 |
| EP | 1736197 | 12/2006 |
| EP | 1736198 | 12/2006 |
| EP | 1736199 | 12/2006 |
| EP | 1870126 | 12/2007 |
| EP | 1985263 | 10/2008 |
| EP | 2070494 A1 | 6/2009 |
| EP | 2095798 | 9/2009 |
| JP | 2119877 | 5/1990 |
| JP | 8107934 | 4/1996 |
| WO | 9220519 A1 | 11/1992 |
| WO | 9422520 | 10/1994 |
| WO | 9640357 | 12/1996 |
| WO | 9701370 | 1/1997 |
| WO | 9920338 | 4/1999 |
| WO | 9926543 | 6/1999 |
| WO | 9934859 | 7/1999 |
| WO | 0015158 A1 | 3/2000 |
| WO | 0033901 | 6/2000 |

(56) References Cited

FOREIGN PATENT DOCUMENTS

| | | |
|---|---|---|
| WO | 0110359 A1 | 2/2001 |
| WO | 0149245 A2 | 7/2001 |
| WO | 0180926 | 11/2001 |
| WO | 0195813 A1 | 12/2001 |
| WO | 0210667 A2 | 2/2002 |
| WO | 02074381 | 9/2002 |
| WO | 03105732 A1 | 12/2003 |
| WO | 2004016971 | 3/2004 |
| WO | 2005037055 A2 | 4/2005 |
| WO | 2005072627 A1 | 8/2005 |
| WO | 2006021695 | 3/2006 |
| WO | 2009007526 | 1/2009 |
| WO | 2009129474 A1 | 10/2009 |
| WO | 2011137036 A1 | 11/2011 |
| WO | 2012061355 A1 | 5/2012 |
| WO | 2012068190 A1 | 5/2012 |

OTHER PUBLICATIONS

Geim AK. et al.; 'Microfabricated Adhesive Mimicking Gecko Foot-Hair'; Nature Materials Abstract only; vol. 2; No. 7; 2003.

Yamagami, Takuji; 'Technical Developments; Use of Targeting Guide Wire in Left Subclavian Puncture During Percutaneous Implantation of Port-Catheter Systems Using the Catheter Tip Fixation Method' European Radiology; vol. 13; pp. 863-866; 2003.

Yurdumakan B., et al.; 'Synthetic Gecko Foot-Hairs from Multiwalled Carbon Nanotubes'; The Royal Society of Chemistry; p. 3799-3801; 2005.

Helioscopie Product Insert for Heliogast, pp. 1-11 (undated).

http://en.wikipedia.org/wiki/Injection.sub.--molding, Dated : Mar. 20, 2014.

\* cited by examiner

IMPLANTABLE DEVICE TO PROTECT TUBING FROM PUNCTURE

RELATED APPLICATIONS

This application is a continuation of U.S. patent application Ser. No. 13/019,238, filed Feb. 1, 2011, which is a continuation-in-part of U.S. patent application Ser. No. 12/771,609, filed on Apr. 30, 2010, the entire disclosures of which are incorporated herein by reference.

FIELD

The present invention generally relates to medical systems and apparatus and uses thereof for treating obesity and/or obesity-related diseases, and more specifically, relates to an implantable device used in a medical system to protect tubing from puncture.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan. Inc., Irvine, Calif.) gastric band or the LAP-BAND AP® (Allergan. Inc., Irvine, Calif.) gastric band. Generally, gastric bands are placed about the cardia, or upper portion, of a patient's stomach forming a stoma that restricts the food's passage into a lower portion of the stomach. When the stoma is of an appropriate size that is restricted by a gastric band, food held in the upper portion of the stomach provides a feeling of satiety or fullness that discourages overeating. Unlike gastric bypass procedures, gastric band apparatus are reversible and require no permanent modification to the gastrointestinal tract.

Certain types of gastric band systems may operate through a hydraulic force. The size of the band placed around the stomach may depend on the volume of the fluid in the band. An access port may be used to control the amount of fluid in the band. The access port may be located below the surface of an individual's skin. The physician accesses the access port to either increase or decrease the amount of fluid in the band. The physician inserts a long hypodermic needle through the surface of the skin and into the access port. The physician may then deposit or remove fluid from the system to control operation of the gastric band. However, the access port may be under many layers of fat, and may be difficult to locate. If the physician cannot properly locate the access port, the physician may improperly insert the hypodermic needle into the individual's body.

If the physician improperly inserts the hypodermic needle into the individual's body, the hypodermic needle may puncture the tube leading from the access port to the gastric band. The tube contains fluid that may leak causing the gastric band to eventually fail. The entire gastric band system may then need to be removed from the individual's body, or the physician may need to perform an operation to mend the punctured tube.

SUMMARY

Generally described herein is an implantable shielding device that protects tubing used in a gastric band system. A protective system placed over the tubing may protect the tube from errant needle sticks.

In one embodiment, the implantable device comprises an access port configured to attach to body tissue, a tube coupled to the access port, and a shielding device coupled to the tube. The shielding device is positioned adjacent to the access port and covers the end of the tube coupled to the access port. The shielding device is made from a puncture resistant material. The shielding device protects the tube from puncture, by blocking the movement of a needle directed towards the tube.

In one embodiment, the shielding device comprises a plurality of individual shields. Each individual shield may have a bell-like shape, a cone-like shape, a cylindrical shape, a bullet-like shape, or a ball and socket shape. The individual shields are positioned adjacent to each other along the tube. Each individual shield may be independently moveable to allow the tube to bend. Portions of adjacent individual shields overlap each other to assure no portion of the tube is exposed to an incoming needle. In addition, multiple different shapes of individual shields may be alternatively placed along the tube.

In one embodiment, the shielding device comprises a coil wrapped around the outer circumference of the tube. The coil is wrapped such that no portion of the tube is exposed to the needle. The coil may include a single wire, or multiple wires wrapped around the tube. In addition, multiple layers of wire may be wrapped over each other around the tube to further assure a needle cannot puncture the tube. Furthermore, the coil may have a size that is small enough to be integrated within the tube, as an alternative to placing it around the tube. The coil may be made from metal or a hard plastic or polymer.

In one embodiment, the shielding device has a flattened disk-like shape and is coupled to the access port. The flattened disk extends outward from the access port in a radial dimension to cover a portion of the tube. The shielding device may comprise multiple flattened disks extending outward from the access port, or a half-disk shape extending from the access port in a direction towards the tube. In addition, the shielding device may have multiple layers of material pressed together or sandwiched together to increase puncture resistance. The flattened disk may be a flexible disk, made from a flexible puncture resistant fabric or a hard material such as plastic.

The present invention includes a shielding device for shielding from and preventing needle puncture to a tubing for the conduct of a fluid, the tubing extending between and for providing bi-directional passage of a fluid between a subcutaneously implantable access port and a hydraulically inflatable portion of a gastric band, the gastric band intended for circumscribing the stomach of an obese patient. In one embodiment, the shielding device includes a substantially spiral-shaped body portion. The spiral-shaped body portion forms wraps around the tube. An extended portion of the shielding device extends from the body portion, and covers the portion of the tube positioned between adjacent wraps of the body portion. The body portion and/or the extended portion may be made of a puncture resistant material or materials.

DETAILED DESCRIPTION

The present invention relates to a shielding device that protects a tube or tubing used in a gastric band system. Specifically, the shielding device protects a tube or tubing from puncture by a syringe needle inserted near the tube or tubing.

Figure 1:
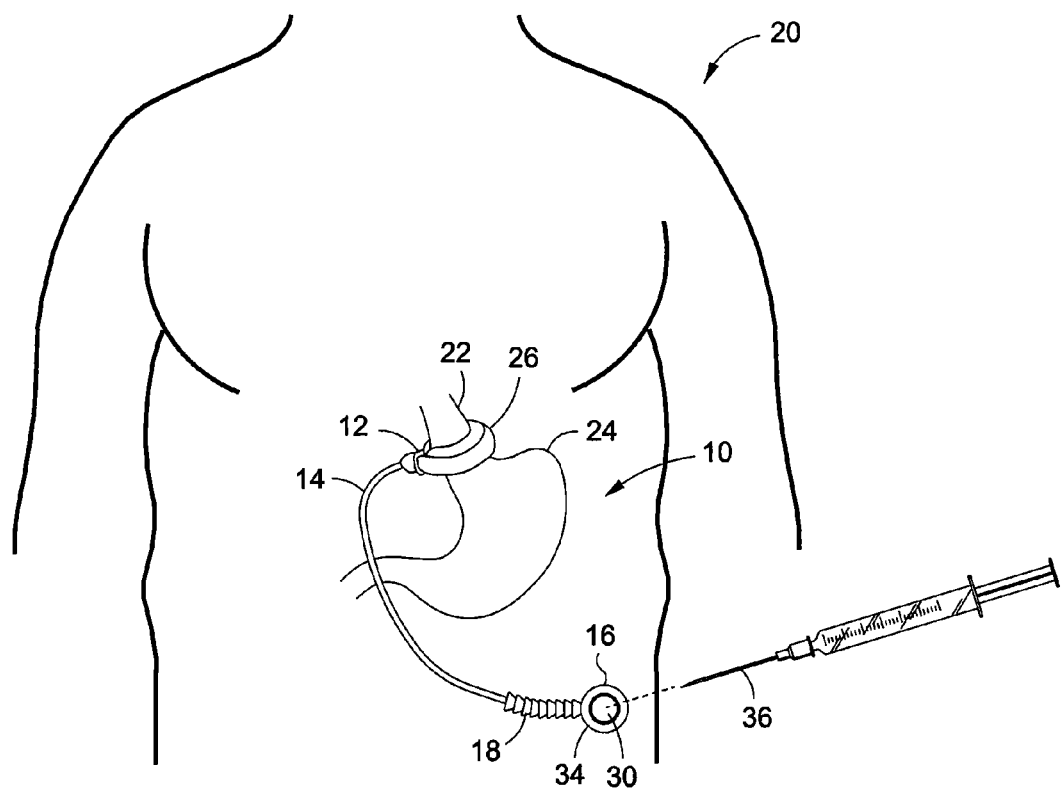
FIG. 1 illustrates a gastric band system according to an embodiment of the present invention.

As shown in FIG. 1, the gastric band system 10 includes a band 12 (e.g., a gastric band 12), a tube 14, an access port 16, and a shielding device 18 placed over a portion of the tube 14. The gastric band system 10 is surgically implanted within an individual's body 20. A physician places the band 12 around the upper portion 22 of an individual's stomach 24 and fixes the access port 16 to a portion of the individual's body 20. Preferably, the access port 16 is securely fixed to the muscle wall of the abdomen inside the individual's body 20. The tube 14 connects the band 12 to the access port 16. The shielding device 18 is positioned completely around the tube 14, adjacent to the access port 16.

The gastric band system 10 shown in FIG. 1 operates in response to a hydraulic force. The band 12 includes an inner bladder 26 defining an inner diameter 28 (shown in FIG. 2) with a size that varies based on the volume of fluid inside the inner bladder 26. The volume of fluid inside the inner bladder 26 may be controlled by a physician through the access port 16. The access port 16 may include a septum 30, a fluid chamber 32 (shown in FIG. 8), and an access port housing 34 holding the fluid chamber 32 and the septum 30. The septum 30 is configured as a membrane located over the fluid chamber 32, to allow a syringe needle 36 to pass through the septum 30 and into the fluid chamber 32 to deposit or remove fluid. The septum 30 is preferably made from a soft needle-penetrable material such as silicone. The tube 14 has two ends, with one end coupled to the fluid chamber 32 and one end coupled to the inner bladder 26 of the band 12. The tube 14 transfers the fluid from the fluid chamber 32 to the inner bladder 26 of the band 12. In this configuration, a physician can control the size of the inner bladder 26 by inserting a syringe needle 36, or long hypodermic needle, through the surface of the individual's skin, through the septum 30, and into the fluid chamber 32, to either deposit or inject fluid into or remove fluid from the gastric band 12.

If the physician deposits or injects fluid into the fluid chamber 32, the inner bladder's 26 inner diameter 28 decreases, and the band 12 constricts the upper portion 22 of the stomach 24. The constricted upper portion 22 of the stomach 24 reduces the flow of food passing to the lower part of the stomach 24, ideally causing the individual to lose weight over time. If the physician removes fluid from the fluid chamber 32, the inner bladder's 26 inner diameter 28 increases, and band 12 loosens around the upper portion 22 of the stomach 24. The flow of food passing to the lower part of the stomach 24 correspondingly increases.

Figure 2:
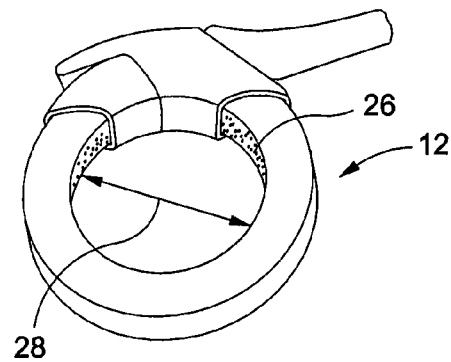
FIG. 2 illustrates a perspective view of the inner diameter of the band corresponding to a decreased volume of fluid in the gastric band according to an embodiment of the present invention.

FIG. 2 illustrates an increased size of the inner diameter 28 corresponding to a decreased volume of fluid in the inner bladder 26 of the gastric band 12.

Figure 3:
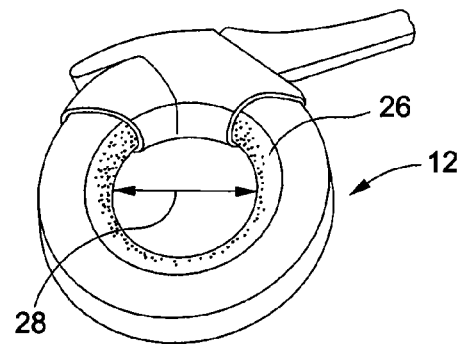
FIG. 3 illustrates a perspective view of the inner diameter of the band corresponding to an increased volume of fluid in the gastric band according to an embodiment of the present invention.

FIG. 3 illustrates a decreased size of the inner diameter 28 corresponding to an increased volume of fluid in the inner bladder 26 of the gastric band 12.

Figure 4:
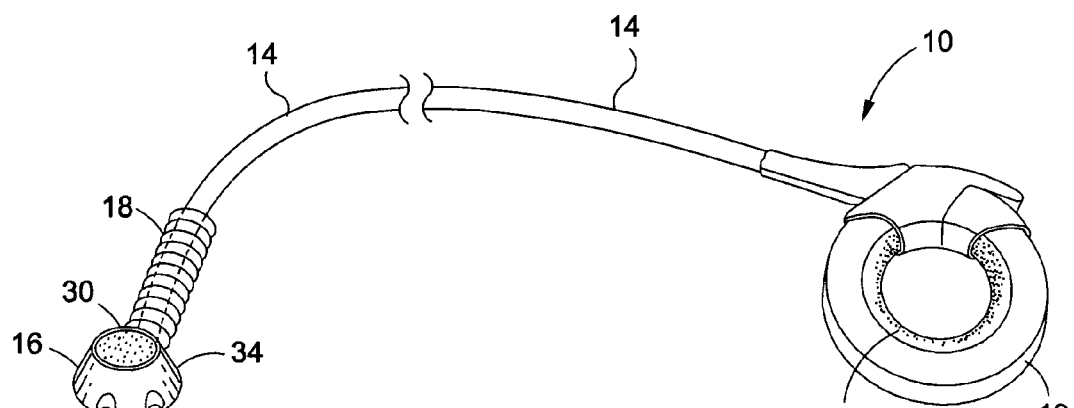
FIG. 4 illustrates a perspective view of the gastric band system removed from an individual's body according to an embodiment of the present invention.

FIG. 4 illustrates a perspective view of the gastric band system 10 when it is not installed within the interior of the individual's body 20.

To adjust the size of the inner bladder 26, the physician may need to repeatedly insert a syringe needle 36 into the individual's body 20 to add or remove fluid from the gastric band system 10. Also, the physician may need to insert a syringe needle 36 on a periodic basis to adjust the size of the inner bladder 26, or to assure the fluid pressure is sufficient in the gastric band system 10. As such, it is important that the physician be able to easily identify and locate the precise position of the septum 30.

Figure 5:
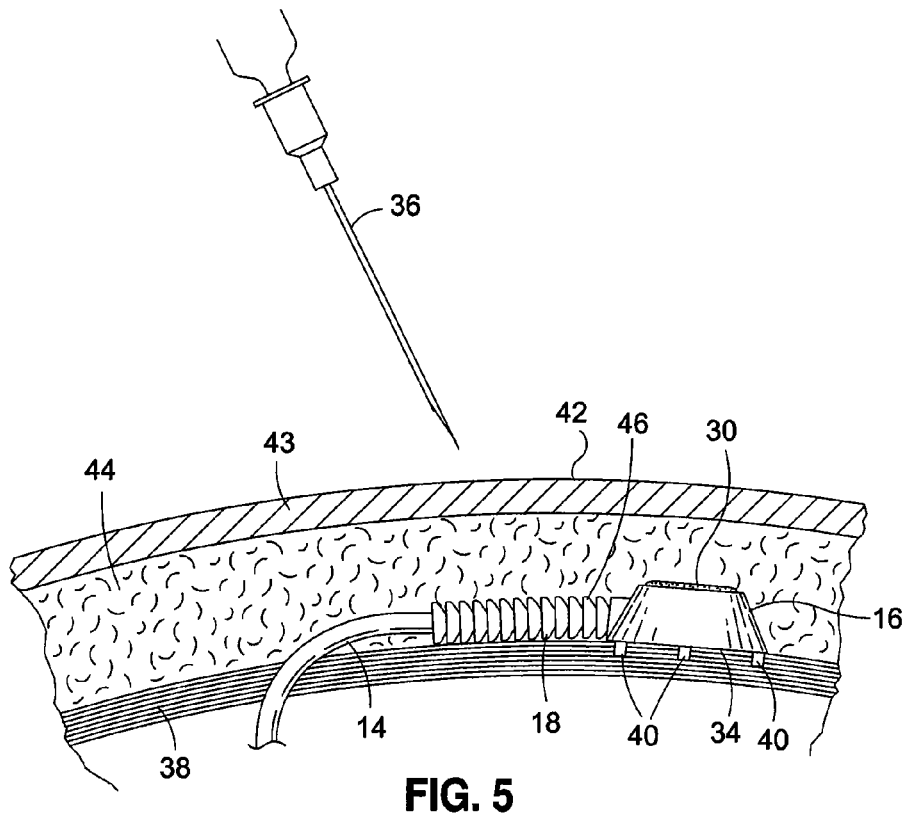
FIG. 5 illustrates a side, cut-away view of the access port attached to the muscle wall of an individual according to an embodiment of the present invention.

FIG. 5 shows a side, cut-away view of the access port 16 attached to or engaged with the abdominal muscle wall 38 of the individual. As discussed above, a physician may surgically implant the access port 16 to the muscle wall 38 of an individual. The muscle wall 38 provides a secure attachment point to assure the access port 16 does not travel throughout the individual's body 20 and potentially disengage from the tube 14. The access port 16 is configured to attach to bodily tissue. A plurality of anchors 40 may be used to fix the access port 16 to the muscle wall 38. These anchors 40 may comprise hooks or barbs that penetrate the muscle wall 38 and fix the access port 16 in place.

When the physician attaches the access port 16 to the muscle wall 38, the physician also passes the tube 14 inside the individual's body 20 to connect to the inner bladder 26. The tube 14 should remains flexible to allow the physician to easily manipulate the tube 14 during insertion. Accordingly, the tube 14 may be made of a durable, flexible material such as silicone or other equivalent material.

A drawback to fixing the access port 16 to the muscle wall 38 is that the position of the septum 30 may change over time relative to the surface 42 of the skin 43. The amount of fat 44 located around the access port 16 may vary, shifting the position of the access port 16 relative to the surface 42 of the skin 43. In this situation, the physician may not be able to detect the exact position of the septum 30. Therefore, it may be difficult for the physician to repeatedly determine the exact position of the septum 30 over an extended period of time, if the patient's weight is changing. A physician can place a mark on the skin 43 to indicate the position of the septum 30; however, the mark may deviate from the septum 30 over time. To properly locate the septum 30, the physician can also palpate the area around the access port 16 to generally feel where the septum 30 is located. However, even a skilled physician may not correctly determine the precise location of the septum 30 because it may be under many layers of fat 44.

The physician may therefore incorrectly insert the syringe needle 36 through the skin 43 and contact the muscle wall 38. Although this result may be painful, another problem may occur if the syringe needle 36 penetrated the tube 14. As discussed above, the tube 14 is typically made from a soft, flexible material such as silicone, which may be easily penetrated by a syringe needle 36. If the tube 14 is punctured, the pressurized fluid in the tube 14 may leak out into the individual's body 20. The gastric band system 10 would then be inoperable, and the physician would either need to surgically remove the gastric band system 10 or perform an operation to mend the punctured tube 14. To alleviate the problem of a punctured tube 14, the shielding device 18 may be placed over a portion of the tube 14 located adjacent to the access port 16. In one embodiment, the shielding device 18 is placed completely around the tube 14 so that the tube 14 is protected from all sides and directions.

Figure 6:
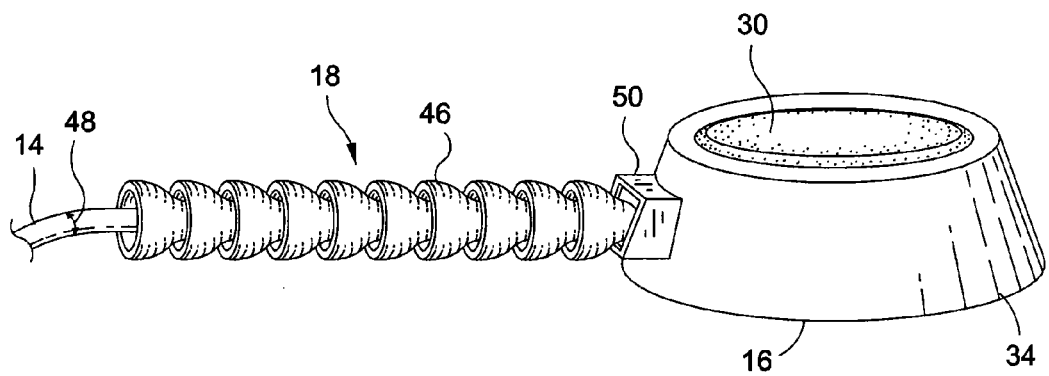
FIG. 6 illustrates a perspective, close-up view of the shielding device and the access port according to an embodiment of the present invention.

FIG. 6 displays a perspective view of one embodiment of the shielding device 18. The shielding device 18 may comprise a plurality of individual shields 46, or beads, coupled to the tube 14 and spaced adjacent to one another. Each individual shield 46 has a generally cylindrical shape that entirely wraps around an outer circumference 48 of the tube 14. Each individual shield 46 may be made from a hard, puncture resistant material that is impenetrable by the needle 36 inserted by the physician. The material may be a hard plastic, a light-weight metal, a ceramic, or a hardened polymer, or a thermoplastic such as polysulfone. Generally, the material is hard enough that the syringe needle 36 is incapable of piercing the puncture resistant material, beyond merely placing a small divot or scratch on the surface of the material. The shielding device 18 covers the end of the tube 14 and is positioned close enough to the access port 16 to block a misplaced needle 36 inserted by the physician. For example, the shielding device 18 may be attached to and positioned adjacent to the access port housing 34 such that no gap exists between the shielding device 18 and the access port housing 34. In addition, the access port housing 34 may include a protective canopy structure 50 to assure a needle 36 traveling towards the tube 14 cannot contact an area of exposed tube 14 between the shielding device 18 and the access port housing 34. The shielding device 18 protects the tubing from needle sticks while remaining flexible and provides strain relief for the tubing.

Figure 7:
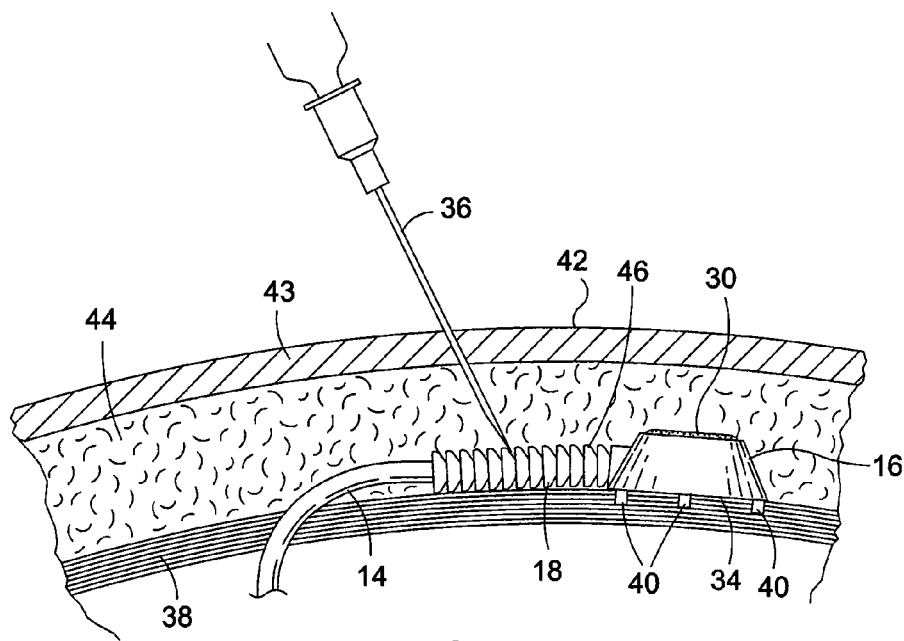
FIG. 7 illustrates a side, cut-away view of the shielding device in operation according to an embodiment of the present invention.

The operation of the shielding device 18 is shown in FIG. 7. When a physician inserts the needle 36, the shielding device 18 blocks the motion of the needle 36 and prevents it from penetrating the tube 14. Because the shielding device 18 is made from a hard material, the physician may feel the syringe needle 36 hit a hard surface and will know the needle 36 is not contacting the septum 30. The physician may then retract the syringe and attempt to find the septum 30 again. The tube 14 will be protected from puncture.

In an alternative operation, the shielding device 18 may be composed of a puncture resistant material that merely resists penetration by a needle 36. The puncture resistant material may deform when contacted by the needle 36, but the energy required to pass through the shielding device 18 and contact the tube 14 may be great. The physician will notice the increased resistance and realize the needle 36 is not contacting the septum 30.

Figure 8:
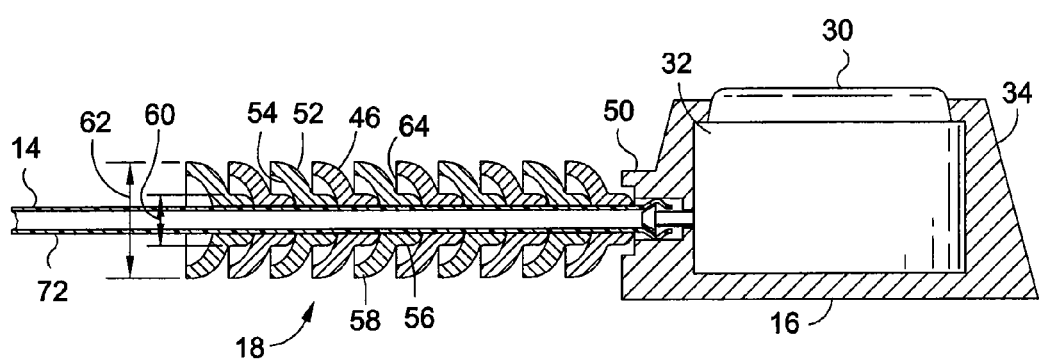
FIG. 8 illustrates a side, cross-sectional view of the shielding device according to an embodiment of the present invention.

FIG. 8 illustrates a cross-section view of the shielding device 18 showing the shape and position of each individual shield 46 along the tube 14. In this embodiment, each individual shield 46 has a generally bell-like shape, with a curved outer surface 52 and curved inner surface 54. Each individual shield 46 has a neck portion 56 and an extended portion 58. Both the neck portion 56 and extended portion 58 have an associated diameter, with the diameter 60 of the neck portion 56 being smaller than the diameter 62 of the extended portion 58. The different diameters 60, 62 allow the extended portion 58 to form a hollow cavity 64 defining the inner surface 54. Thus, the extended portion 58 defines the hollow cavity 64 for receiving the neck portion 56 from an adjacent shield 46. The neck portion 56 of an adjacent individual shield 46 may enter into a portion of the hollow cavity 64. The neck portion 56 and the extended portion 58 of the adjacent individual shields 46 therefore overlap slightly and are moveably connected to one another. The curved shape of the outer surface 52 and the inner surface 54 allow the neck portion 56 to more easily enter the hollow cavity 64. The neck portion 56 of an individual shield 46 enters into the hollow cavity 64 to assure a syringe needle 36 cannot directly contact the tube 14 if it is inserted in a perpendicular direction towards the tube 14. If the extended portion 58 does not extend over the neck portion 56 of the adjacent individual shield 46, a small gap of exposed tube 14 may exist between the individual shields 46. The needle 36 can then penetrate the tube 14 at the exposed areas.

Figure 9:
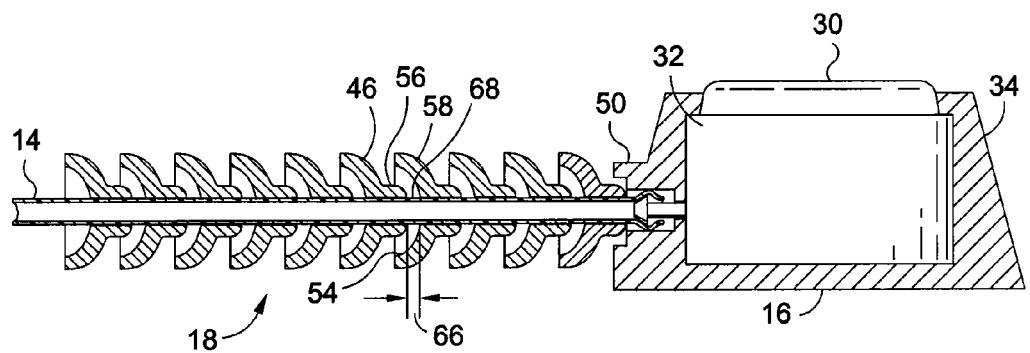
FIG. 9 illustrates a side, cross-sectional view of the shielding device according to an embodiment of the present invention.

The individual shields 46 are spaced along the tube 14 equidistantly, at regular intervals from each other. However, the spacing between the individual shields 46 may vary in different embodiments. In the embodiment shown in FIG. 8, each individual shield 46 is spaced such that the neck portion 56 contacts or very nearly contacts the inner surface 54 of an adjacent individual shield 46. In this configuration, no gap exists between the adjacent individual shields 46. However, in the embodiment shown in FIG. 9, the individual shields 46 may be spaced such that a small gap 66 exists between the neck portion 56 of an individual shield 46 and the inner surface 54 of an adjacent individual shield 46. The gap 66 increases the flexibility of the portion of the tube 14 protected by the shielding device 18. The gap 66 may be formed by gluing the individual shields 46 at a distance from each other, or spacers may be used, as discussed in relation to FIG. 22. As discussed above, it may be beneficial to have the tube 14 be flexible during insertion into an individual 20. A size or shape of the extended portion 58 of an individual shield 46 may be modified to assure the exposed tube portion 68 between the individual shields 46 is still protected from an incoming needle 36.

Figure 10:
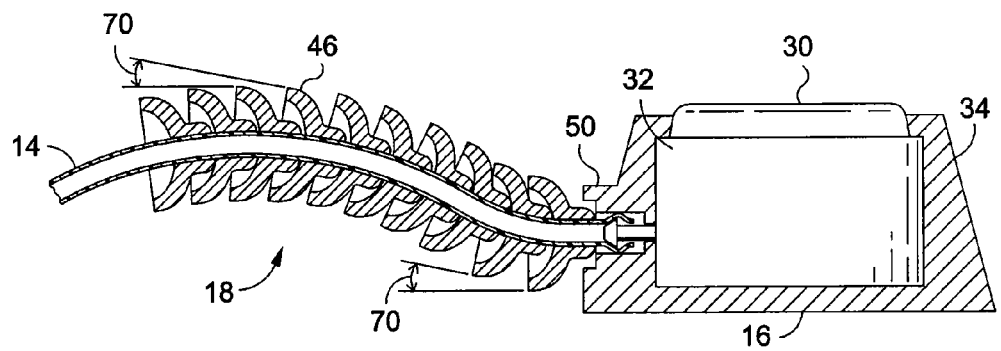
FIG. 10 illustrates a side, cross-sectional view of the shielding device according to an embodiment of the present invention.

FIG. 10 illustrates the flexibility of the shielding device 18 for the embodiment shown in FIG. 8. Each individual shield 46 may rotate with respect to the position of an adjacent individual shield 46. The angle of rotation 70 may be based on a plurality of factors, including the length and shape of the extended portion 58, the distance of the individual shields 46 to each other, and the overall flexibility of the material comprising the tube 14 and the individual shields 46. The flexibility of the shielding device 18 is an advantage over an embodiment simply including a hard metal or plastic sheath placed over a portion of the tube 14. A hard sheath placed over a portion of the tube 14 would not allow a physician to easily manipulate the tube 14 when inserted into an individual 20. The plurality of individual shields 46 allow a hard, inflexible, material to be attached to the tube 14, yet allow the tube 14 to remain flexible for easy manipulation. In addition, a flexible tube 14 is also important for patient comfort. For example, if the patient were to bend over, a rigid shielding device may exert more pressure on the surrounding tissues than a flexible one, resulting in pain.

Referring back to FIG. 8, each individual shield 46 may be individually coupled to the outer surface 72 of the tube 14. In one embodiment, the individual shields 46 are not directly coupled to each other but rather coupled to the outer surface 72 of the tube 14. The individual shields 46 may be slid onto the tube 14 and then fixed in place along the tube 14 with silicone glue or other equivalent attachment means. An individual shield 46 may therefore not slide along the tube 14 or move laterally relative to another individual shield 46. The individual shields 46 may be immovably fixed to the tube 14. In addition, if the individual shields 46 are coupled directly to the tube 14, the access port housing 34 does not need to be modified. The tube 14 may be disengaged from the access port housing 34, and the shielding device 18 will remain attached to the tube 14.

However, in one embodiment, the individual shields 46 may be fixed to the tube 14 in another manner. For example, each individual shield 46 may be fixed to a flexible sleeve (not shown), and the flexible sleeve may be slid over the tube 14. The flexible sleeve may be directly attached to the access port housing 34 or glued to the outer surface 72 of the tube 14. The flexible sleeve may allow the shielding device 18 to be entirely disengaged from the tube 14 and the access port housing 34 during assembly or disassembly of the gastric band system 10.

Figure 11:
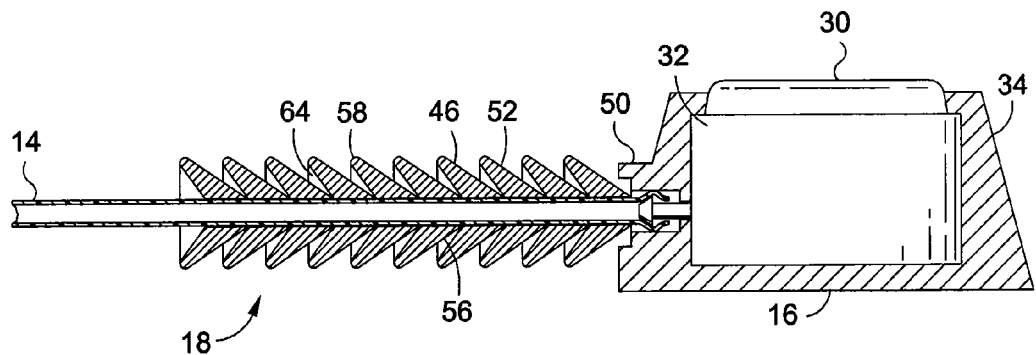
FIG. 11 illustrates a side, cross-sectional view of the shielding device according to an embodiment of the present invention.

FIG. 11 illustrates a cross-sectional view of an embodiment of the shielding device 18 with each individual shield 46 having a generally cone-like shape. Similar to the embodiment shown in FIG. 8, each individual shield 46 has a neck portion 56 and an extended portion 58. However, in this embodiment, the outer surface 52 of the individual shield 46 has a flattened shape, and the hollow cavity 64 has a conical shape. The neck portion 56 of the individual shield 46 extends into the extended portion 58 of an adjacent individual shield 46. Similar to the embodiment shown in FIG. 8, the overlap of the extended portion 58 over the neck portion 56 protects the tube 14 from contact with an incoming syringe needle 36. In addition, similar to the embodiment shown in FIG. 8, the size of an extended portion 58 and the distance between adjacent individual shields 46 may be varied to offer different levels of flexibility and protection for the tube 14.

Figure 12:
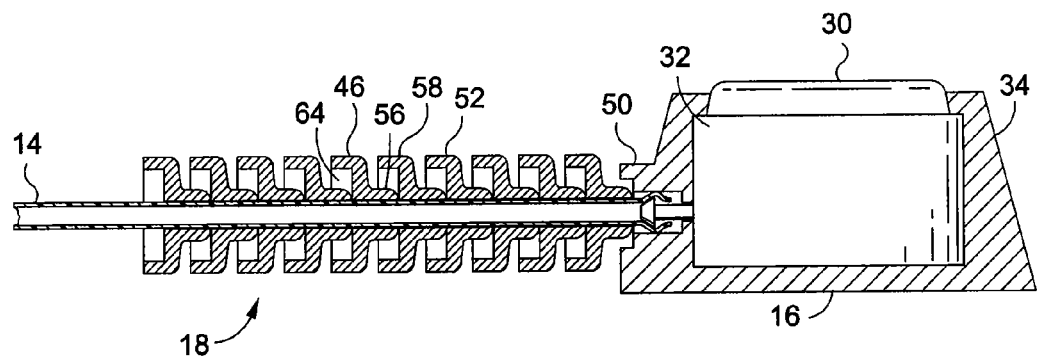
FIG. 12 illustrates a side, cross-sectional view of the shielding device according to an embodiment of the present invention.

FIG. 12 illustrates a cross-section view of an embodiment of the shielding device 18 with each individual shield 46 having a more cylindrical shape than the embodiment shown in FIG. 8. Similar to the embodiment shown in FIG. 8, each individual shield 46 has a neck portion 56 and an extended portion 58. However, in this embodiment, the outer surface 52 of the individual shield 46 has a more flattened shape, and the hollow cavity 64 has a cylindrical shape. The neck portion 56 of the individual shield 46 extends into the extended portion 58 of an adjacent individual shield 46. Similar to the embodiment shown in FIG. 8, the overlap of the extended portion 58 over the neck portion 56 protects the tube 14 from contact with an incoming syringe needle 36. In addition, similar to the embodiment shown in FIG. 8, the size of an extended portion 58 and the distance between adjacent individual shields 46 may be varied to offer different levels of flexibility and protection for the tube 14.

Figure 13:
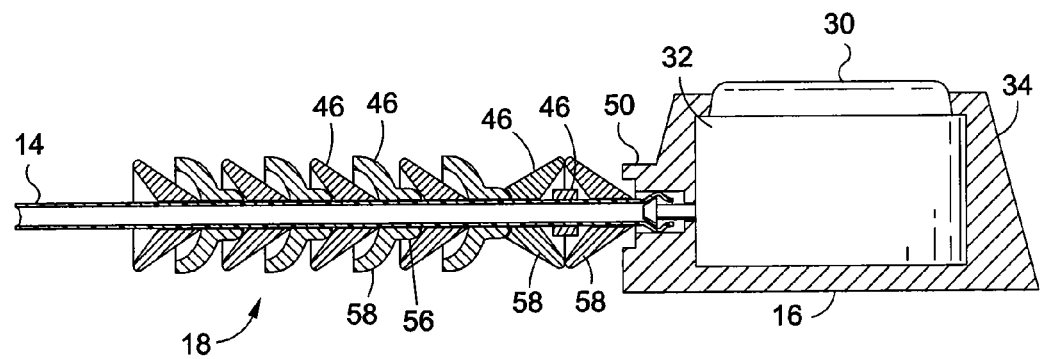
FIG. 13 illustrates a side, cross-sectional view of the shielding device according to an embodiment of the present invention.

FIG. 13 illustrates one embodiment of the shielding device 18 utilizing a combination of cone-shaped individual shields 46 and bell-shaped individual shields 46. The cone-shaped individual shields 46 and bell-shaped individual shields 46 may be alternatively placed along the length of the tube 14. In addition, similarly shaped individual shields 46 may be placed in a different orientation with respect to one another. For example, a cone-shaped individual shield 46 may have an extended portion 58 directed towards an extended portion 58 of an adjacent cone-shaped individual shield 46. The embodiment shown in FIG. 13 also illustrates an individual shield 46 may have no defined extended portion 58 or neck portion 56. As shown in FIG. 13, the shape, orientation, and position of the individual shields 46 may be varied to produce alternative degrees of flexibility and protection for the tube 14.

Figure 14:
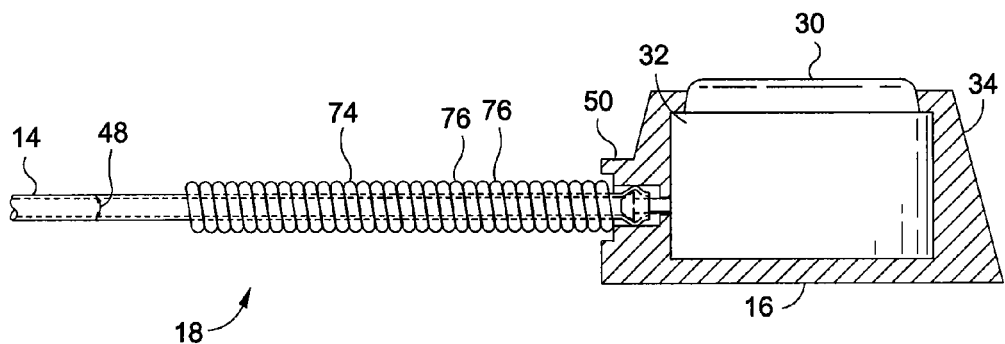
FIG. 14 illustrates a side view of the shielding device according to an embodiment of the present invention.

FIG. 14 illustrates an embodiment of the shielding device 18 utilizing a wire or hard tubing wrapped multiple times over a portion of the tube 14, forming a coil 74. The coil 74 encircles the exterior circumference 48 of the tube 14. The coil 74 may be comprised of a hard material, such as a metal wire, or a flexible hard plastic or polymer. The metal may comprise titanium, nitinol, other non-ferrous relatively flexible materials, or a similar biocompatible metal.

The coil 74 is positioned adjacent to the access port housing 34, to leave no gap between the coil 74 and the access port housing 34 for a syringe needle 36 to contact the tube 14. In addition, the tightly wound wraps 76 of the coil 74 are spaced closely, and may contact each other, to leave no gap for a syringe needle 36 to pass through the shielding device 18 and contact the tube 14.

The multiple wraps 76 of the coil 74 allow the shielding device 18 to remain flexible, yet still be comprised from a hard material. A wrap 76 of the coil 74 may rotate relative to an adjacent wrap 76 of the coil 74. The coil 74 may be fixed to the tube 14 directly, through a silicone glue or equivalent means of fixing the coil 74. In addition, a portion of the coil 74 may be coupled directly to the access port housing 34, to further secure the coil 74 in place along the tube 14.

Figure 15:
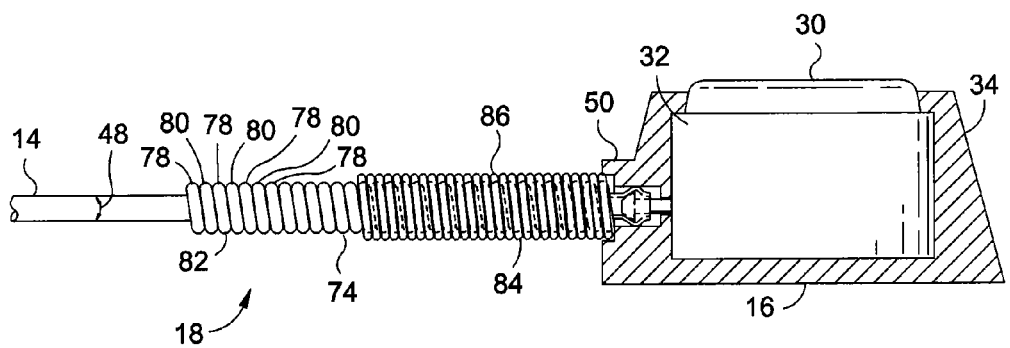
FIG. 15 illustrates a side, close-up view of the shielding device according to an embodiment of the present invention.

FIG. 15 illustrates an embodiment of the shielding device 18 shown in FIG. 14 utilizing two different wires 78, 80 wrapped around the tube 14 to form an inner coil 82. A secondary or outer coil 84 is also placed over and around the inner coil 82. The secondary coil 84 is wrapped multiple times around an exterior circumference of the inner coil 82. The two different wires 78, 80 may be wrapped alternatively around the tube 14. The wraps may be spaced near each other or in direct contact with each other. It is beneficial to utilize two wires 78, 80 if, for example, one of the wires 78, 80 breaks. The other wire may hold the coil 74 in place around the tube 14. In addition, each wire 78, 80 may be composed of a different material. One wire may be made from a more flexible material and one wire may be made from a material that is harder but less flexible. The different materials may provide a varying amount of flexibility and strength for the coil 74.

The secondary coil 84 comprises a wire 86 wrapped over the surface of the inner coil 82. The wire 86 of the secondary coil 84 includes wraps positioned close to or in contact with each other. The wire 86 of the secondary coil 84 may have a narrower diameter than a wire 78, 80 of the inner coil 82 to allow the secondary coil 86 to more easily flex when the tube 14 is manipulated. The secondary coil 84 may be placed along the entire length of the inner coil 82 or over a portion of the inner coil 82 adjacent to the access port housing 34. Although FIG. 15 illustrates three wires 78, 80, 86 wrapped around the exterior circumference 48 of the tube 14, many more layers or many more wires may be used to form a coil 74 around the tube 14.

Figure 16:
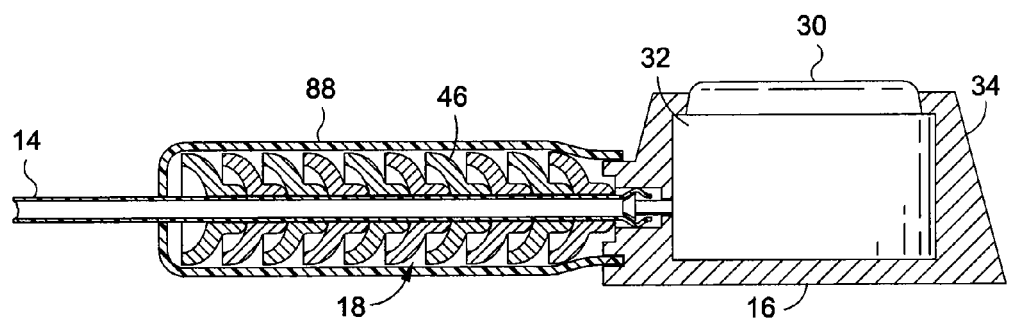
FIG. 16 illustrates a side, cross-sectional view of the shielding device according to an embodiment of the present invention.

FIG. 16 illustrates an embodiment of the shielding device 18 including a cylindrical sheath 88 placed over the entirety of the shielding device 18. The cylindrical sheath 88 may comprise an overmolding of silicone placed over the shielding device 18. The silicone overmolding may provide a greater degree of biocompatibility for the shielding device 18 and provides further strain relief for the tube 14. In addition, the cylindrical sheath 88 may smooth the surface of the shielding device 18 to allow the tube 14 to be more easily inserted into an individual's body 20. The cylindrical sheath 88 may be combined with any of the embodiments discussed herein, including the embodiments shown in FIGS. 17 and 20.

Figure 17:
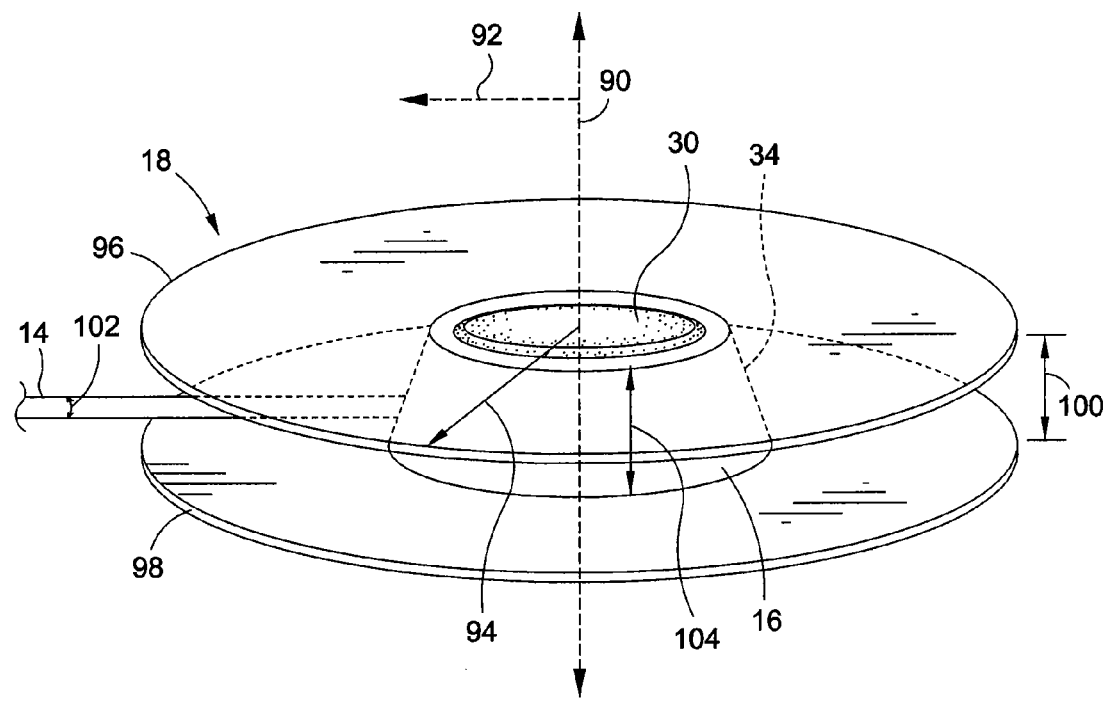
FIG. 17 illustrates a perspective view of the shielding device according to an embodiment of the present invention.

FIG. 17 illustrates an embodiment of the shielding device 18 having a flattened disk-like or skirt-like shape. In this configuration, the shielding device 18 is fixed directly to the access port housing 34. The access port housing 34 may define a radial dimension 92 and an axial dimension 90. The shielding device 18 extends from the access port housing 34 in a radial direction, and in the radial dimension 92, away from the access port housing 34. The shielding device 18 covers the end of the tube 14 from a syringe needle 36 traveling towards the tube 14. The size of the radius 94, or distance from the access port 16, formed by the shielding device 18 determines the extent of the tube 14 covered by the shielding device 18. In one embodiment, the size of the radius 94 may be greater than twice a diameter of the access port 16. In the embodiment shown in FIG. 17, the shielding device 18 may include two disks, a top disk 96 and a bottom disk 98. The end of the tube 14 passes between the two disks 96, 98. The distance 100 between the top disk 96 and bottom disk 98 may define the flexibility of the tube 14 and the amount of protection for the tube 14. For example, if the two disks 96, 98 are placed relatively near each other (e.g., spaced at the diameter 102 of tube 14), then the tube 14 may be trapped between the two disks 96, 98 and cannot move too much. However, the disks 96, 98 protect the tube 14 from a needle 36 passing towards the tube 14 at a relatively horizontal angle relative to the access port housing 34. If the disks 96, 98 are placed relatively far from each other (e.g., spaced at the height 104 of the access port housing 34), the tube 14 may be more flexibly manipulated, but the disks 96, 98 offer less protection from the needle 36 being able to pass toward the tube 14 horizontally. The shielding device 18 may also comprise a single top disk 96 placed above the tube 14 to protect the tube from a needle 36 traveling in an axial direction.

The disk-like or skirt-like shaped shielding device 18 allows the tube 14 to be shielded without any attachment or modification to the tube 14, unlike the embodiment shown in FIG. 8. The tube 14 retains its flexibility, only limited by the dimensions of the shielding device 18, as discussed above. However in this embodiment, the access port housing 34 is modified. The shielding device 18 may be firmly fixed to the access port housing 34 or removably fixed to the access port housing 34. If the shielding device 18 is removably fixed, it may be snap-fit to an outer portion of the access port 16. The shielding device 18 may be made out of a puncture resistant material, including a hard plastic, metal, ceramic, or hard polymer. In addition, the shielding device 18 may be made from a fabric material such as several layers of a tightly woven nylon or polyester, woven quartz or silica fibers, or the equivalent. The fabric material provides puncture resistance, but also allows the shielding device 18 to flex or bend to conform to the patient's body, or allow for easy insertion into the patient's body. Thus, the shielding device 18 may comprise a flexible disk-like or skirt-like shaped device. In addition, each disk 96, 98 may comprise a single layer of a puncture resistant material, or multiple layers of a puncture resistant material compressed or sandwiched together.

Figure 18:
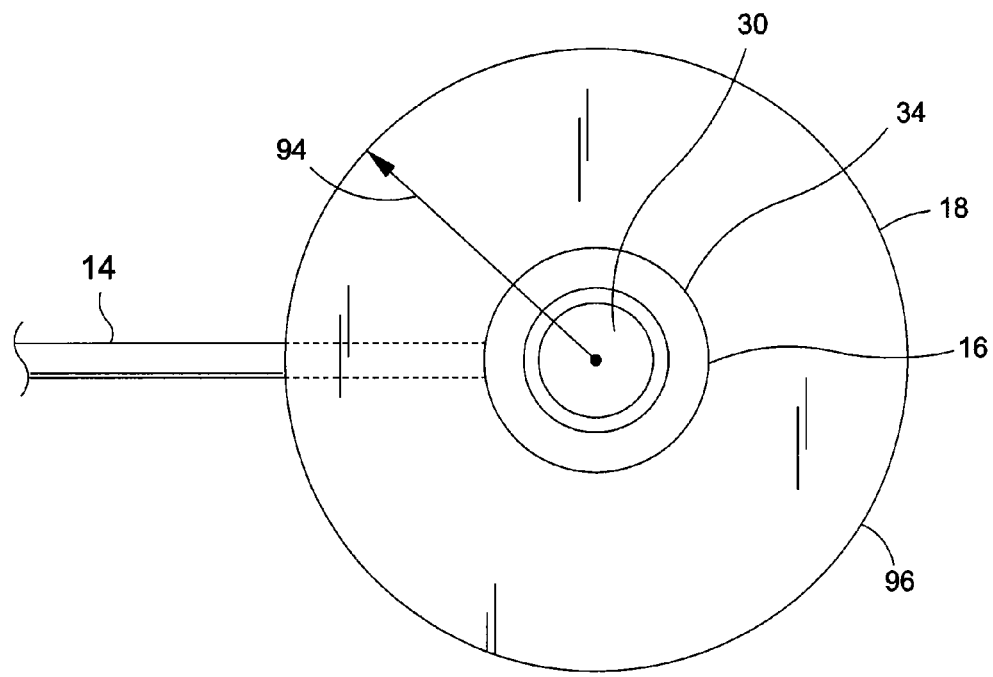
FIG. 18 illustrates a top view of the shielding device according to an embodiment of the present invention.

FIG. 18 illustrates a top view of the shielding device 18 as shown in FIG. 17. The top view illustrates the shielding device 18 extending out radially from the access port 16 and covering a portion of the tube 14. The shielding device 18 extends radially around the entirety of the access port 16, or, in other words, 360 degrees around the axis of the axial dimension 90 shown in FIG. 17.

Figure 19:
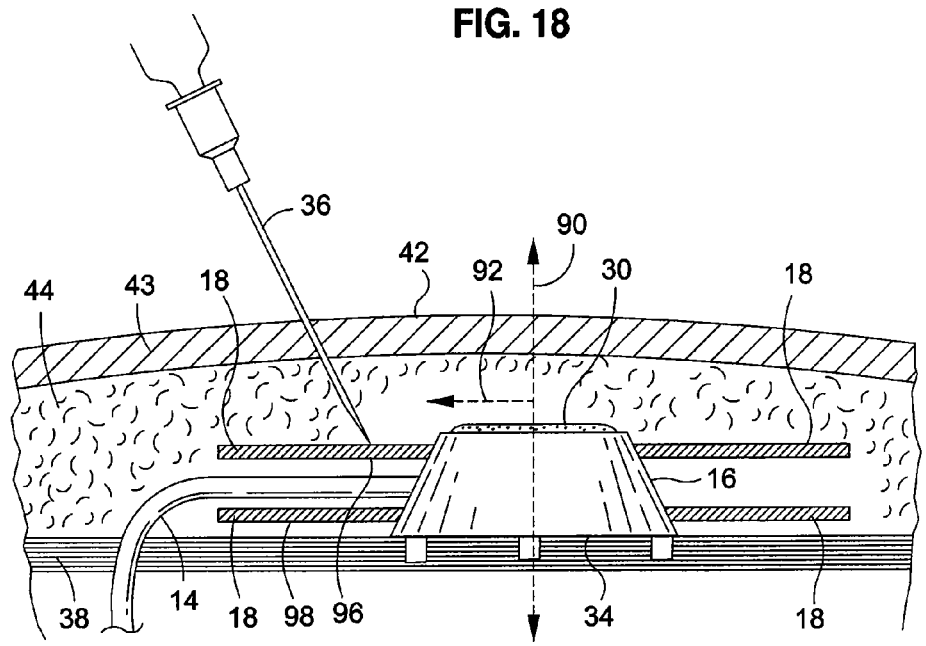
FIG. 19 illustrates a side, cut-away view of the shielding device in operation according to an embodiment of the present invention.

FIG. 19 illustrates the shielding device 18 in operation. Similar to the operation of the shielding device 18 shown in FIG. 8, if a physician incorrectly inserts a syringe needle 36 towards the tube 14, the needle 36 may contact the shielding device 18. The physician may notice the syringe needle 36 has contacted a hard material, and will know the needle 36 did not contact the septum 30. The tube 14 will not be punctured.

Figure 20:
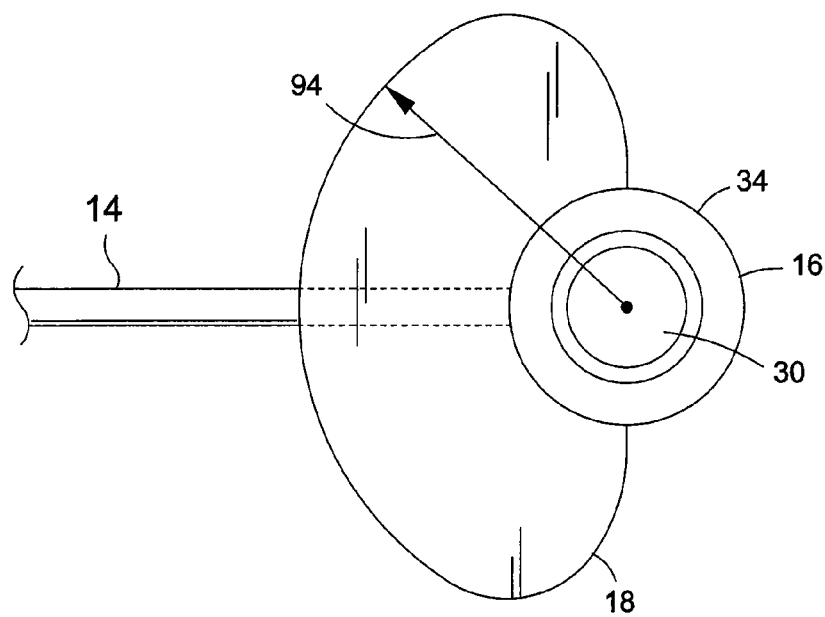
FIG. 20 illustrates a top view of the shielding device according to an embodiment of the present invention.

FIG. 20 illustrates a top-view of an alternate shape of the shielding device 18 shown in FIG. 17. In this embodiment, the shielding device 18 may have a disk-like shape that does not extend radially around the entirety of the access port housing 34. The shielding device 18 only extends radially in a direction (i.e., one direction) towards the tube 14, and only extends radially around a portion of the access port 16 (e.g., half of the access port housing 34, or 180 degrees around axis of the axial dimension 90 shown in FIG. 17). The modified disk shape, or half-disk shape, may offer less protection for the tube 14 around the entire access port housing 34. However, the half-disk shape also provides the access port housing 34 with a smaller total size. The smaller size may make it easier for a physician to insert the access port 16 into an individual's body.

Figure 21:
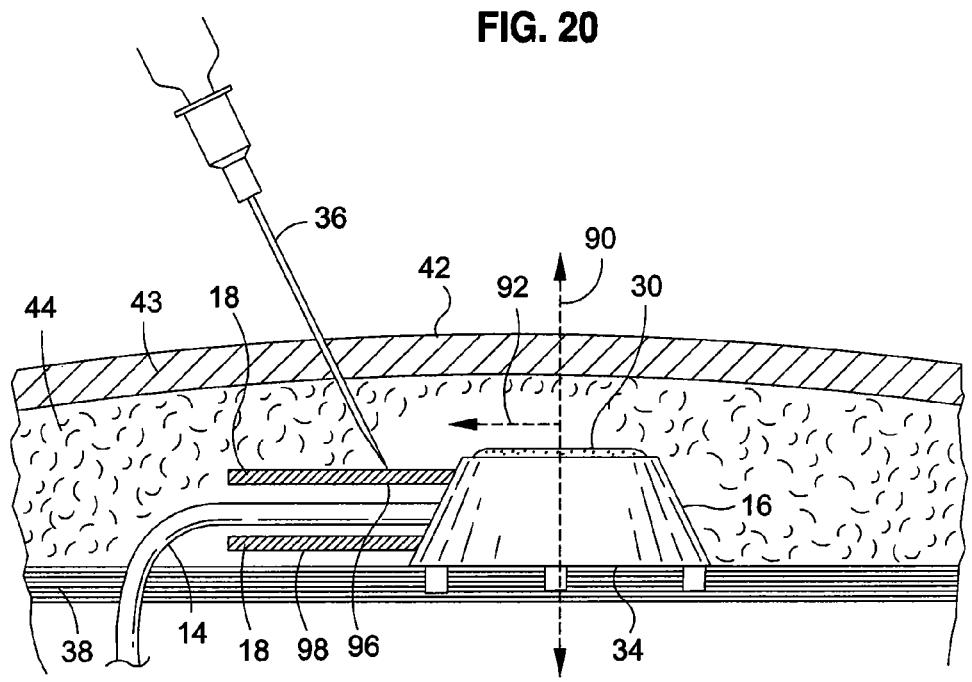
FIG. 21 illustrates a side, cut-away view of the shielding device in operation according to an embodiment of the present invention.

FIG. 21 illustrates the shielding device 18 shown in FIG. 20 in operation. The shielding device 18 blocks a syringe needle 36 from contacting the tube 14. The shielding device 18 in this embodiment only extends around a portion of the access port housing 34 in a direction towards the tube 14.

Figure 22:
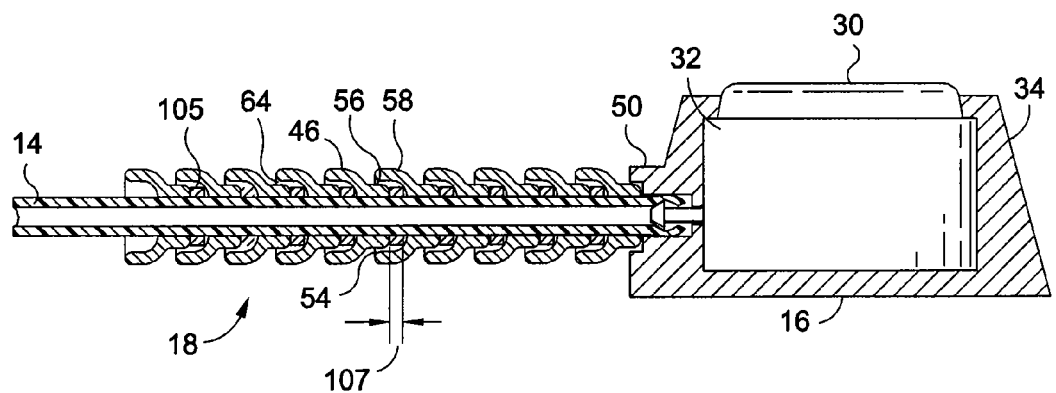
FIG. 22 illustrates a side, cross-sectional view of the shielding device according to an embodiment of the present invention.

FIG. 22 illustrates an embodiment of the shielding device 18 including spacers 105 that have an annular shape, placed between the individual shields 46. The spacers 105 may extend entirely around the outer surface of the tube 14 and may be positioned between the individual shields 46. The spacers 105 may be positioned within the hollow cavity 64 that is defined by the extended portion 58. A width 107 of the spacer 105 may be used to define a distance between the individual shields 46. The spacers 105 may be made of a pliable material, such that the spacers 105 may compress when the individual shields 46 are rotated with respect to each other. Such pliable material may include a soft plastic or the like. In addition, the spacers 105 may also be made of a hard material, but may be sized small enough to still allow the individual shields 46 to rotate. The spacers 105 may have a variety of shapes, including, but not limited to an o-ring shape, a tubular shape, or a toroid shape. The spacers 105 are used to space the shields 46 from each other. In addition, the spacers 105 may also provide protection for the tube 14, and may be made from a needle impenetrable material. The spacer 105 may be designed to protect the exposed areas of the tube 14 positioned between the individual shields 46. The spacers 105 may be firmly fixed to the tube 14 in any manner discussed previously in this application.

Figure 23:
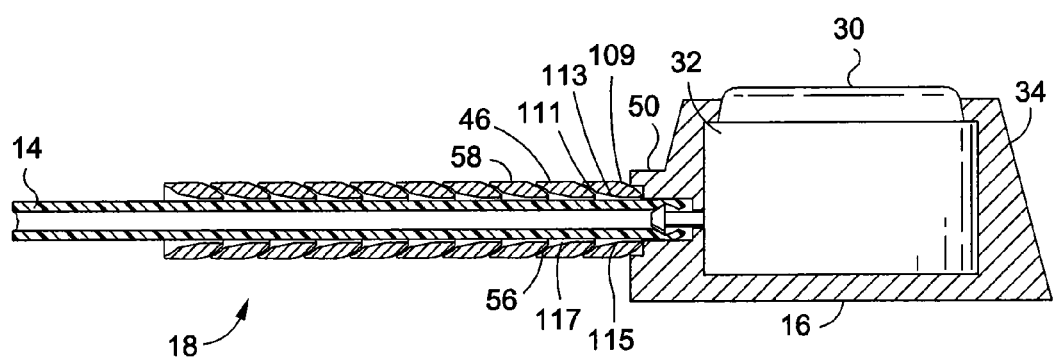
FIG. 23 illustrates a side, cross-sectional view of the shielding device according to an embodiment of the present invention.

FIG. 23 illustrates an embodiment of the shielding device 18 including bullet-like shaped individual shields 46. In this embodiment, each individual shield 46 has an external articulating surface 109, an internal articulating surface 111, a cylindrical surface 115, and a conical surface 113. The portion of the shield 46 near the cylindrical surface 115 generally comprises the neck portion 56 of the shield 46. The portion of the shield 46 positioned near the internal articulating surface 111 generally comprises the extended portion 58 of the individual shield 46. In this embodiment, the internal articulating surface 111 extends over the external articulating surface 109 of an adjacent shield. In this manner, the two surfaces 111, 109 form a congruent fit around the circumference of the tube 14. The two surfaces 111, 109 may contact each other, to assure a syringe needle cannot penetrate through a gap in the shielding device 18. The two surfaces 111, 109 may have a corresponding arc shapes, or curved shapes, that may allow them to contact each other with a substantial amount of surface area.

The cylindrical surface 115 is shaped to wrap around the tube 14, and may grip the tube or may be glued directly to the tube 14. In addition, the cylindrical surface 115 may be slightly larger than the tube 14. The shielding device 18 in this embodiment remains flexible, in part, because of the conical surface 113 positioned between the internal articulating surface 111 and the cylindrical surface 115. A portion of the conical surface 113 may be shaped to extend in a direction away from the surface of the tube 14 with a generally conical shape. One end of the conical surface 113 is positioned near the tube 14 and another end extends away from the tube 14. The end of the conical surface 113 positioned away from the tube 14 transitions to the internal articulating surface 111, which, as discussed above, has a curved shape to conform to a curved or arc shape of the external articulating surface 109.

The shape of the conical surface 113 forms an interior cavity 117 positioned between the tube 14 and the individual shield 46. The interior cavity 117 allows the individual shield 46 to rotate, or articulate around the tube 14 when the tube 14 is flexed. No portion of an adjacent individual shield 46 extends into the interior cavity 117.

When the tube 14 is flexed, the internal articulating surface 111 and the external articulating surface 109 slide with respect to one another and compress or expand a portion of the interior cavity 117. The arc shape of the surfaces 111, 109 aids the sliding motion of the shields 46. In addition, when the tube 14 is flexed, one portion of the external articulating surface 109 slides away from the respective portion of the internal articulating surface 111, and a portion of the external articulating surface 109 slides towards the respective portion of the internal articulating surface 111 simultaneously. The two portions of the external articulating surface 109 may be positioned opposite from one another around the individual shield 46. The external articulating surface 109 and the internal articulating surface 111 remain in contact, or remain close to one another when the tube 14 is flexed. This configuration allows for a closely guarded, yet flexible tube 14. The design eliminates the need for spacers between the shields 46 and minimizes any gaps between the shields 46. The sizes or particular shapes of the individual shields 46 in this embodiment may be varied to produce alternative, equivalent results. The individual shields 46 may be firmly fixed to the tube 14 in any manner discussed previously in this application.

Figure 24:
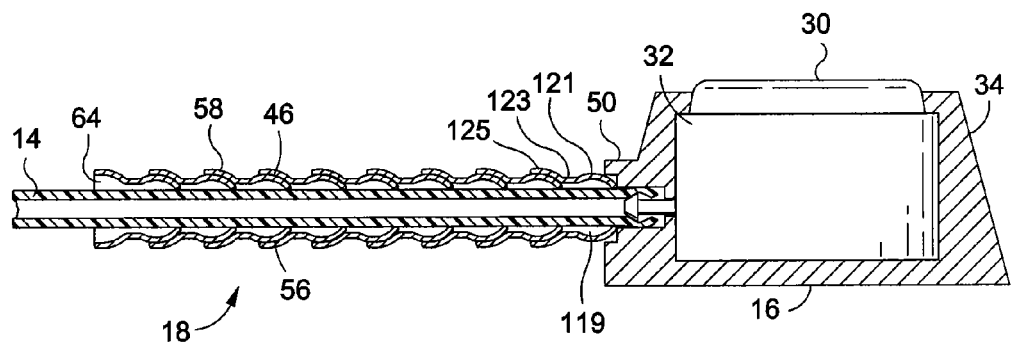
FIG. 24 illustrates a side, cross-sectional view of the shielding device according to an embodiment of the present invention.

FIG. 24 illustrates an embodiment of the shielding device 18 including ball and socket shaped individual shields 46. In this embodiment, each individual shield 46 has an external spherical surface 121, a narrow portion 123, and a spherical housing portion 125. The spherical housing portion 125 extends around the external spherical surface 121 and has a curved, spherical shape corresponding to a curved, spherical shape of the external spherical surface 121. Thus, the spherical housing portion 125 may contact or nearly contact the external spherical surface 121. The spherical shape of both the spherical housing portion 125 and the external spherical surface 121 allow the connection between the two components 125, 121 to serve as a ball joint, allowing the tube 14 to flex, or rotate substantially. Each individual shield 46 may rotate with respect to an adjacent individual shield 46, limited by the extent that the spherical housing portion 125 wraps around the external spherical surface 121. In other words, if the housing portion 125 wraps entirely around the external spherical surface 121, then no rotation will be possible. In this embodiment, the external spherical surface 121 comprises the neck portion 56 of the individual shield 46, and the spherical housing portion 125 comprises the extended portion 58.

The rotation of the spherical housing portion 125 is limited by the narrow portion 123, which is positioned between the external spherical surface 121 and the spherical housing portion 125. The narrow portion 123 serves as a transition point between the external spherical surface 121 and the housing portion 125. If the individual shield 46 rotates too far in one direction, a portion of the spherical housing portion 125 contacts the narrow portion 123, preventing further movement.

The individual shields 46 additionally remain flexible around the tube 14 because the ball and socket shape forms a ball cavity 119, within the interior of the individual shield 46. The ball cavity 119 provides an area of movement for the individual shield 46, similar to the internal cavity 117 shown in FIG. 23. Thus, portions of the ball cavity 119 may be variably distanced from the surface of the tube 14 during movement of the tube 14. The ball cavity 119 may be formed because the external spherical surface 121 may only contact the tube 14 at a narrow portion, or a ring portion of the external spherical surface 121. Thus, the ball cavity 119 extends outward from the surface of the tube 14. The ring portion may be firmly fixed to the tube 14 in any manner discussed previously in this application.

Similar to the embodiment shown in FIG. 23, this configuration allows for a closely guarded, yet flexible tube 14. The design eliminates a need for spacers between the shields 46 and minimizes any gaps between the shields 46. The sizes or particular shapes of the individual shields 46 in this embodiment may be varied to produce alternative, equivalent results.

Figure 25:
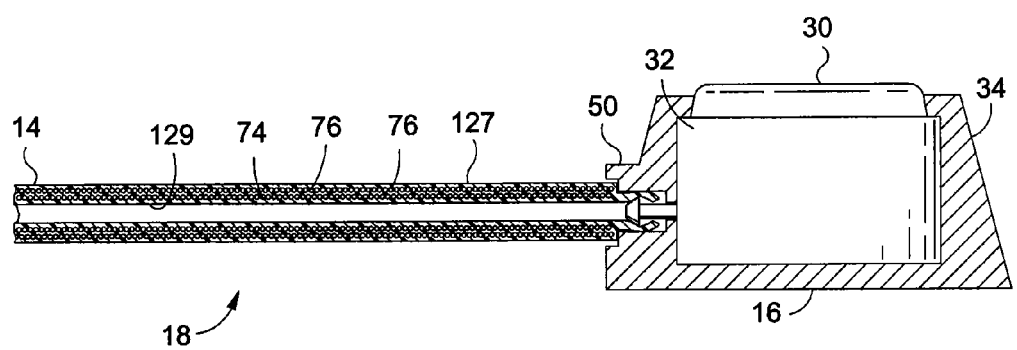
FIG. 25 illustrates a side, cross-sectional view of the shielding device according to an embodiment of the present invention.

FIG. 25 illustrates an embodiment of the shielding device 18 including a coil 74 wrapped around an interior surface 129 of the tube 14. This configuration is similar to the embodiment shown in FIG. 14, but in this embodiment, the coil 74 is positioned within the tube 14. In other words, the coil 74 is small enough to fit within an exterior surface 127 of the tube 14, yet is large enough to extend around an interior surface 129 of the tube 14. The multiple wraps 76 of the coil 74 entirely encircle the interior surface 129 or interior circumference of the tube 14. The benefit of this embodiment is to reduce the size of the shielding device 18 to equal, or nearly equal the diameter of the tube 14 without a shielding device 18 attached. The tube 14 including the coil 74 would then have an overall smaller cross section than the embodiment shown in FIG. 14. This may be advantageous to allow a physician to more easily insert the tube into a patient's body.

Although FIG. 25 illustrates the tube 14 sized larger than the tube shown in FIG. 14, the sizing is for illustrative purposes only. In this embodiment, the tube 14 may have an equal total diameter, or smaller total diameter than shown in FIG. 14. In addition, the coil 74 may extend along only a portion of the tube 14 or may extend along the entirety of the tube 14 (e.g., from one end near or touching the housing 34 to the other end near or touching the gastric band 12). In addition, similar to the embodiment shown in FIGS. 14 and 15, the coil 74 may include multiple wraps of wire, multiple layers of wire wraps, or multiple wires wrapped around the interior surface 129 of the tube 14. The coil 74 in this embodiment, similar to the embodiment shown in FIG. 14, may be made from a metal such as titanium, nitinol or a hard plastic. The coil 74 may be molded into the tube 14 or fixed to the interior surface 129 of the tube 14 through any manner discussed above in relation to FIGS. 14 and 15.

Figure 26:
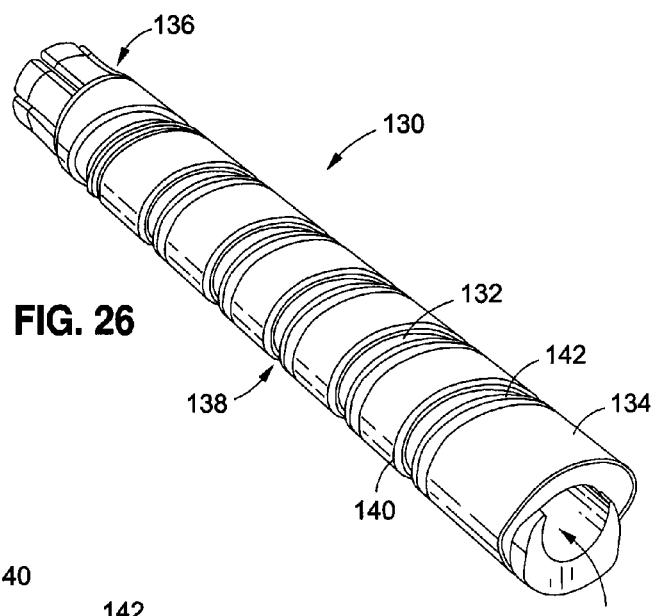
FIG. 26 illustrates a perspective view of a shielding device according to an embodiment of the present invention.
Figure 29:
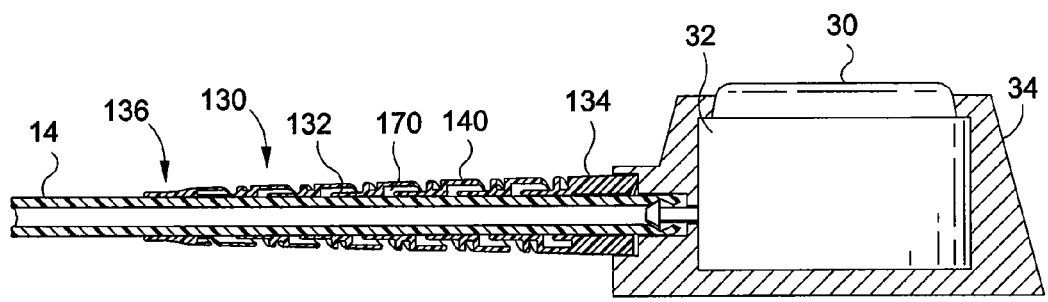
FIG. 29 illustrates a side, cross-sectional view of a shielding device according to an embodiment of the present invention.

FIG. 26 illustrates a front perspective view of an embodiment of a shielding device 130 including a substantially spiral-shaped body portion 132 configured to wrap around the tube 14 (for example the tube 14 shown in FIG. 29). The shielding device 130 comprises a tapered cross-section, swept along a helix, to create a spiral geometry that is flexible, yet has no exposed gaps that allow a needle to penetrate the tube 14. The shielding device 130 has a connecting end 134 and a compliant end 136 and a middle portion 138 comprising the portion of the shielding device 130 that lies between the two ends 134, 136. An extended portion 140 of the shielding device 130 extends from the body portion 132 and has a spiral shape, to form an overlapping section of the shielding device 130. A ridge 142 extends from the body portion 132 and has a spiral shape. The wraps of the body portion 132 form a cylindrical shaped channel 144 through the interior of the shielding device 130 for the tube 14 to pass through.

Figure 27:
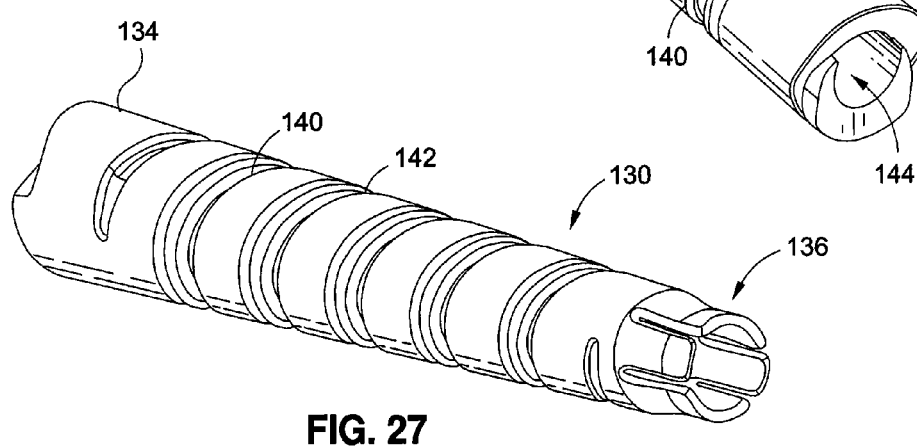
FIG. 27 illustrates a perspective view of a shielding device according to an embodiment of the present invention.

FIG. 27 illustrates a rear perspective view of the shielding device 130 shown in FIG. 26.

Figure 28:
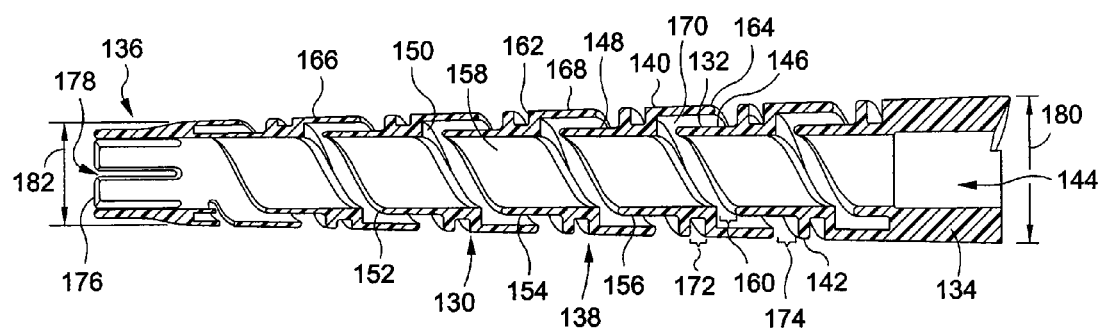
FIG. 28 illustrates a side, cross-sectional view of a shielding device according to an embodiment of the present invention.

FIG. 28 illustrates a side cross-sectional view of the shielding device 130 shown in FIGS. 26 and 27. The body portion 132 is a spiral or helical shaped structure that is configured to wrap multiple times around the tube 14 (for example the tube 14 shown in FIG. 29). The wraps are configured to be positioned adjacent to each other in succession along the length of the tube 14. Each wrap, for example a first wrap 146 and a second wrap 148, comprises a complete loop of the body portion 132 around the tube 14.

The body portion 132 has a leading edge 150 and a trailing edge 152 that are configured to spiral continuously around the tube 14. A flattened band-like middle section 154 of the body portion 132 connects the leading edge 150 to the trailing edge 152. The middle section 154 has a flattened outer surface 156. An inner surface 158 of the middle section 154 has a flattened shape, and is configured to face towards the tube 14.

The leading edge 150 and trailing edge 152 of adjacent wraps of the body portion 132 are separated by a gap 160. The gap 160 between adjacent wraps has a spiral shape due to the spiral configuration of the body portion 132. The gap 160 may have a length between approximately 0.020 to 0.050 inches, although this length may be varied as desired.

An extended portion 140 extends from the body portion 132 to cover the gap 160 positioned between adjacent wraps of the body portion 132. The extended portion 140 is structured to extend outward from the leading edge 150 of the body portion and extend over at least a portion of the gap 160, or entirely over the gap as shown in FIG. 28. The extended portion 140 may be structured to extend partially over the part of the body portion 132 forming an adjacent wrap. For example, FIG. 28 illustrates the extended portion 140 of the second wrap 148 extending over a part of the body portion 132 of the first wrap 146.

A trailing edge 162 of the extended portion 140 couples to the leading edge 150 of the body portion 132. The extended portion 140 is thus integrally connected with the body portion 132, as it is made from a unitary piece of material. A leading edge 164 of the extended portion 140 connects to the trailing edge 162 by a middle portion 166 of the extended portion 140. The middle portion 166 has a flattened outer surface 168. The middle portion 166 forms a spiral shaped hollow cavity 170 above the body portion 132. The cavity 170 is formed by an offset between the connection of the trailing edge 162 of the extended portion 140 and the leading edge 150 of the body portion 132. The gap 160 and a portion of the body portion 132 of an adjacent wrap are positioned within the cavity 170.

The spiral shaped ridge 142 comprises a continuous protrusion, or flange, extending from the body portion 132, and being positioned between the two edges 162, 164 of the extended portion 140. For example, FIG. 28 illustrates the ridge 142 of the first wrap 146 extending between the trailing edge 162 of the extended portion 140 of the first wrap 146 and the leading edge 164 of the extended portion 140 of the second wrap 148. The ridge 142 is separated from the trailing edge 162 of the extended portion 140 by a gap 172, and is separated from the leading edge 164 of the extended portion by a gap 174. The ridge 142 serves to strengthen and stiffen the local body portion 132 to which it is fixed.

The connecting end 134 of the shielding device 130 comprises a substantially solid piece of material, in which the extended portion 140 and the body portion 132 are integrated, and the extended portion 140 does not form a cavity 170. The connecting end 134 may be configured in any manner to allow the shielding device 130 to be firmly connected to the access port housing 34 (for example, the access port housing 34 shown in FIG. 29). For example, the connecting end 134 may be keyed to snap fit into the housing 34 (shown in FIG. 29).

The compliant end 136 of the shielding device 130 includes a fluted design having plurality of slats 176 separated by a plurality of slits 178. The slits 178 allows the slats 176 to flex, which provides a degree of flexible compliance for the shielding device 130, to prevent a tube 14 (for example, the tube 14 shown in FIG. 29) extending from the shielding device 130 from kinking as it exits the shielding device 130. The slits 178 and slats 176 enhance the strain relief properties of the shielding device 130.

The connecting end 134 preferably has a diameter 180 being larger than a diameter 182 of the compliant end 136. The middle portion 138 has a substantially tapered profile that smoothly transitions the diameter of the shielding device 130 from end 134 to end 136. In one embodiment, the diameter 180 of the connecting end 134 may be approximately 0.375 inches, and the diameter 182 of the compliant end 136 may be approximately 0.2 inches. The length of the shielding device 130 may be approximately 1.5 to 2 inches. The sizes of the diameters 180, 182, and length of the shielding device 130 may be varied as desired.

The diameter of the shielding device 130 preferably varies linearly from end 134 to end 136, as shown in FIG. 28. The height of the ridge 142 also decreases from end 134 to end 136. In addition, the thickness of the body portion 132 and extended portion 140 may decrease along successive wraps of the body portion 132 from the connecting end 134 to the compliant end 136. The body portion 132 may form as many wraps as desired around the tube 14, to accommodate various desired lengths of the shielding device 130. The shielding device 130 shown in FIG. 28 shows an exemplary number of five wraps of the body portion 132.

FIG. 29 illustrates a cross-section view of the shielding device 130 positioned along the length of the tube 14. The shielding device 130 entirely encircles the tube 14, to protect the tube 14 from errant needle sticks. The connecting end 134 is coupled to the access port housing 34 such that no portion of the tube 14 is exposed between the shielding device 130 and the housing 34. The connecting end 134 may be snapped or clipped to the housing 34. In one embodiment, the shielding device 130 is fixed to the tube 14 directly with an adhesive, for example silicone glue. In one embodiment, the shielding device 130 is overmolded on to the tube 14, or snapped on to the tube 14. In one embodiment, the shielding device 130 may be fixed to a flexible sleeve (not shown) that is slid over the tube 14 and either attached directly to the tube 14 or directly to the housing 34. In one embodiment, the shielding device 130 may be adhered directly to the housing 34, or overmolded to the housing 34. In one embodiment, the shielding device 130 is overmolded to the housing 34 and the tube 14.

The body portion 132 and extended portion 140 of the shielding device are both preferably made of a puncture resistant, yet flexible material. Such materials may include plastics, or polymers, including polysulfone. Any portion of the body portion 132 and/or extended portion 140 may be made of the same puncture resistant material. In addition, a portion of the shielding device 130 may not be made of puncture resistant material, if the shielding device 130 is still capable of providing equivalent shielding performance. Similar to the shielding device 18 discussed in relation to FIG. 7, the puncture resistant material may be capable of entirely blocking movement of an incoming syringe needle, or may merely resist penetration by a needle 36. For example, the puncture resistant material may deform when contacted by a syringe needle, but the energy required to pass through the shielding device 130 and contact the tube 14 may be great. The physician will notice the increased resistance and realize the needle 36 is not contacting the septum 30.

The shielding device 130 operates to protect the tube 14 from errant needle sticks by completely enclosing or covering the tube 14 from incident needles. The portion of tube exposed between adjacent wraps of the body portion 132 is covered by the extended portion 140. The cavity 170 and gap 174 between the leading edge 164 of the extended portion 140 of one wrap, and the ridge 142 of an adjacent wrap (referenced and discussed in relation to FIG. 28) are sized such that a standard sized syringe needle can not pass through the cavity 170, and potentially contact any exposed tube 14.

A benefit of the spiral design of the shielding device 130 is that the device 130 has a unitary construction, which allows the shielding device 130 to be placed over the tube 14 as a single unit. The shielding device 130 could therefore be quickly and easily installed to protect the tube 14. In addition, the shielding device 130 is made flexible, to allow the shielding device 130 to flex during implantation, or after implantation, to enhance a degree of comfort for the patient, similar to the shielding device 18 discussed in relation to FIG. 10. The use of gaps between adjacent wraps of the body portion 132 enhances the flexibility of the shielding device 130, as the grinding action between adjacent wraps that would normally result from a wrapped or spiral design, is reduced. Further, the tapered nature of the shielding device 130 acts enhances the strain relief properties of the shielding device 130, and enhances comfort for the patient and ease of implantation into the patient's body.

Figure 30:
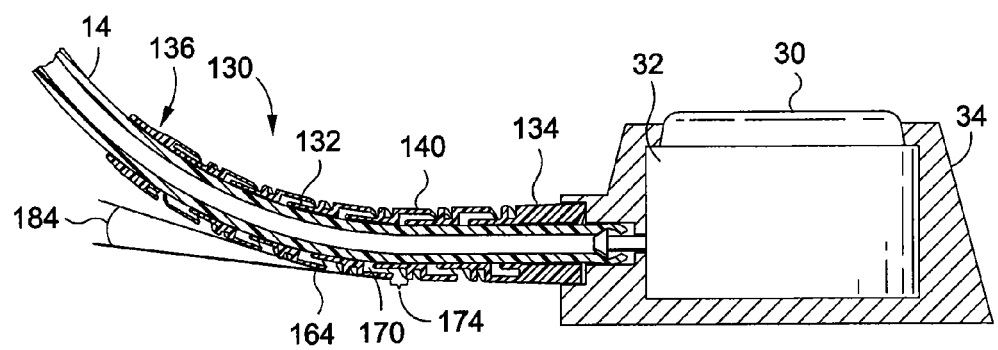
FIG. 30 illustrates a side, cross-sectional view of a shielding device according to an embodiment of the present invention.

FIG. 30 illustrates the flexible properties of the shielding device 130. Adjacent wraps of the body portion 132 may move, or rotate, with respect to each other, forming an angle 184. The angle 184 may reach a maximal value of between seventy and ninety degrees, although this value may be varied as desired. The gap 174 between the ridge 142 and the leading edge 164 of the extended portion 140 is sized to prevent a standard sized syringe needle from passing through the cavity 170. The ridge 142 may be placed or sized to further prevent a syringe from passing through the cavity 170. The tapered profile of the shielding device 130 enhances the flexibility of the shielding device 130, as the portion of the device positioned closer to the compliant end 136 may be capable of flexing more than the portion of the device 130 positioned near the connecting end 134.

Figure 31:
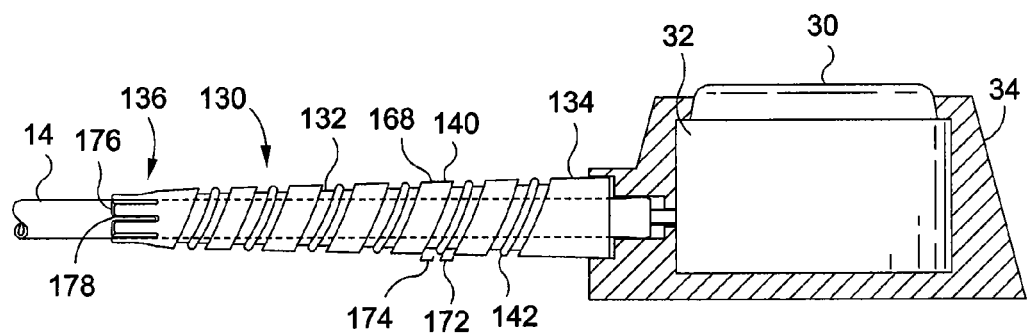
FIG. 31 illustrates a side view of the shielding device according to an embodiment of the present invention.

FIG. 31 illustrates a side view of the shielding device 130 in position along the tube 14. No portion of the tube 14 is exposed by the shielding device 130.

Figure 32:
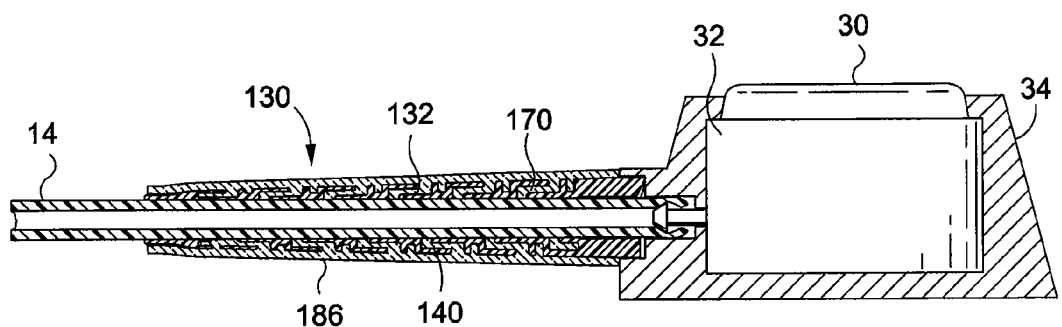
FIG. 32 illustrates a side, cross-sectional view of a shielding device according to an embodiment of the present invention.

FIG. 32 illustrates an overmolding 186 that covers the shielding device 130. The overmolding 186 may be flexible in nature, and comprise an overmolding of an elastomeric material, such as silicone. The overmolding 186 fills in all gaps and cavities of the shielding device 130, forming shielding device 130 having no cavities, notwithstanding the cylindrical shaped channel 144 shown in FIG. 26. The overmolding 186 may enhance the biocompatibility of the device 130, by preventing local tissue from growing into the gaps 172, 174 (referenced in FIG. 31) of the shielding device 130. In addition, the elastomeric material may serve to enhance the overall comfort of the device for the patient. The shielding device 130 may be partially or fully over-molded with various materials, as desired. For example, a membrane of elastomeric material may be formed over the shielding device 130, configured similarly as the sheath 88 shown in FIG. 16.

The spiral shaped shielding device 130 is not limited to the embodiments shown in FIGS. 26-32, but may comprise any desired variation of shielding device 130 that wraps in a spiral and produces an equivalent result. For example, the dimensions of the spiral shaped shielding device 130 may be varied as desired. Various cross-section designs or configurations may be used, that are wrapped in a spiral, to produce varied flexibility and shielding device 130 performance characteristics. In addition, the construction of the compliant end 136 and connecting end 134 may be varied as desired. Further, the shape of the body portion 132, extended portion 140, and/or the cavity 170 formed by the extended portion 140 may appropriately be varied as desired. For example, the winding direction of the wraps may be reversed, or the leading edge 164 of the extended portion 140 may be configured to face the compliant end 136 of the shielding device 130.

In light of the shielding device 18, 130 embodiments disclosed above, the shielding device 18, 130 may be used in a gastric band system 10 that utilizes various components different from those discussed above. For example, a physician may insert the syringe needle to fill a pump reservoir, or maintain a fluid pressure in a mechanical pump system. In addition, a physician may insert a probe near the access port 16 to measure a local property of the gastric band system 10. The shielding device 18, 130 will still serve to protect the tube 14 from puncture in these systems that differ from the gastric band system 10 disclosed above.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of and/or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A shielding device for use to protect a tube from puncture that extends from a subcutaneously implantable access port of a gastric band system for the treatment of obesity, the shielding device comprising:
a substantially spiral-shaped body portion and an extended portion integral with the body portion, the body portion configured to form a first wrap around the tube and a longitudinally adjacent second wrap around the tube, the extended portion structured to extend radially outward from the second wrap and to cover at least a portion of the first wrap and to cover at least a portion of the tube positioned between the first wrap and the second wrap, the body portion being made from a puncture resistant material and the extended portion being made from a puncture resistant material,
wherein the shielding device covers a first end of the tube that is coupled to the subcutaneously implantable access port, the subcutaneously implantable access port comprising a needle-penetrable septum.

2. The shielding device of claim 1 wherein a gap is formed between the first wrap and the second wrap.

3. The shielding device of claim 2 wherein the extended portion extends over the gap.

4. The shielding device of claim 2 wherein the gap has a substantially spiral shape.

5. The shielding device of claim 1 wherein the extended portion has a substantially spiral shape.

6. The shielding device of claim 1 wherein the shielding device is flexible.

7. The shielding device of claim 6 wherein the first wrap is configured to rotate relative to the second wrap.

8. The shielding device of claim 1 wherein the extended portion forms a hollow cavity having a substantially spiral shape.

9. The shielding device of claim 8 wherein a portion of the body portion is positioned within the hollow cavity.

10. The shielding device of claim 1 further comprising a spiral-shaped ridge that extends between the body portion and the extended portion.

11. The shielding device of claim 1 wherein the puncture resistant material of the body portion is plastic, and the puncture resistant material of the extended portion is plastic.

12. The shielding device of claim 1 wherein the shielding device has a first end having a diameter, and a second end having a diameter, and a middle portion, the diameter of the first end being larger than the diameter of the second end, and the middle portion having a tapered shape.

13. The shielding device of claim 12 wherein the second end includes a plurality of slits.

14. The shielding device of claim 1 wherein the extended portion has a substantially flat outer surface.

15. The shielding device of claim 1 wherein the body portion is configured to form at least five wraps around the tube.

16. The shielding device of claim 1 further comprising an overmolding of elastomeric material covering the body portion and the extended portion.

17. An implantable device for use in a gastric band system for the treatment of obesity, the device comprising:
   a subcutaneously implantable access port configured to attach to body tissue, the access port comprising a needle-penetrable septum;
   a tube having a first end and a second end, the first end coupled to the access port; and
   a shielding device covering the first end of the tube and having a substantially spiral-shaped body portion and an extended portion, the body portion configured to form a first wrap around the tube and a second wrap around the tube, the extended portion structured to cover at least a portion of the tube positioned between the first wrap and the second wrap, the body portion being made from a puncture resistant material and the extended portion being made from a puncture resistant material.

18. An implantable device for use in a gastric band system for the treatment of obesity, the device comprising:
   a flexible tubing for the conduct of a fluid, the tubing sized and adapted to extend between a subcutaneously implantable access port comprising a needle-penetrable septum and a hydraulically inflatable portion of a gastric band, the gastric band for circumscribing a portion of a stomach of an obese patient, the flexible tubing for providing bi-directional passage of a fluid between the access port and the gastric band; and
   a substantially spiral-shaped body portion and an extended portion integral with the body portion, the body portion configured to form a first wrap around an end of the tubing located adjacent the access port and a longitudinally adjacent second wrap around the tubing, the extended portion structured to extend radially outward from the second wrap and to cover at least a portion of the first wrap to cover at least a portion of the tubing positioned between the first wrap and the second wrap, the body portion being made from a puncture resistant material and the extended portion being made from a puncture resistant material.

* * * * *